(12) United States Patent
Reb et al.

(10) Patent No.: US 10,695,440 B2
(45) Date of Patent: Jun. 30, 2020

(54) BIOMATERIALS SUITABLE FOR USE AS DRUG ELUTING, MAGNETIC RESONANCE IMAGING DETECTABLE IMPLANTS FOR VASCULAR OCCLUSION

(71) Applicant: Biosphere Medical, Inc., South Jordan, UT (US)

(72) Inventors: Philippe Reb, Themericourt (FR); Celine Chaix, Clichy la Garenne (FR); Meriadeg Thomas, Saint Denis (FR)

(73) Assignee: Biosphere Medical, Inc., South Jordan, UT (US)

( * ) Notice: Subject to any disclaimer, the term of this patent is extended or adjusted under 35 U.S.C. 154(b) by 840 days.

(21) Appl. No.: 13/900,796

(22) Filed: May 23, 2013

(65) Prior Publication Data

US 2013/0315838 A1 Nov. 28, 2013

Related U.S. Application Data

(60) Provisional application No. 61/651,389, filed on May 24, 2012.

(51) Int. Cl.
*A61K 47/69* (2017.01)
*A61K 49/18* (2006.01)

(52) U.S. Cl.
CPC ...... *A61K 47/6927* (2017.08); *A61K 49/1854* (2013.01)

(58) Field of Classification Search
CPC .................. A61K 9/5094; A61K 47/48946
See application file for complete search history.

(56) References Cited

U.S. PATENT DOCUMENTS

| | | | |
|---|---|---|---|
| 5,202,352 A | 4/1993 | Okada et al. | |
| 5,514,379 A | 5/1996 | Weissleder et al. | |
| 6,315,709 B1 | 11/2001 | Garibaldi et al. | |
| 7,407,646 B2 | 8/2008 | Laurent et al. | |
| 2003/0077225 A1 | 4/2003 | Laurent et al. | |
| 2003/0211165 A1 | 11/2003 | Vogel | |
| 2004/0161466 A1* | 8/2004 | Lewis | A61K 9/1635 424/489 |
| 2005/0058603 A1 | 3/2005 | Gao et al. | |
| 2008/0064839 A1* | 3/2008 | Hadba | A61B 17/06166 526/240 |
| 2010/0317113 A1* | 12/2010 | Deshayes | C08F 2/32 435/396 |
| 2011/0076231 A1 | 3/2011 | Schwarz et al. | |
| 2011/0118379 A1* | 5/2011 | Tighe | A61L 27/16 523/113 |
| 2011/0280947 A1 | 11/2011 | Rioux et al. | |
| 2012/0213831 A1 | 8/2012 | Vogel et al. | |

FOREIGN PATENT DOCUMENTS

| | | |
|---|---|---|
| JP | 6056676 A | 1/1994 |
| JP | 2003528130 | 9/2003 |
| JP | 3509858 | 9/2004 |
| JP | 200553707 | 3/2005 |
| WO | 2001072281 | 10/2001 |
| WO | 2001081460 | 11/2001 |
| WO | 2005034912 | 4/2005 |
| WO | 2009073193 | 6/2009 |
| WO | 2011003902 | 1/2011 |
| WO | 2013177364 | 11/2013 |

OTHER PUBLICATIONS

Ceylan et al., J. Applied Polymer Sci., 99, 2006, p. 319-325.*
Notice of Allowance dated Jan. 20, 2016 for U.S. Appl. No. 13/462,004.
Office Action dated Mar. 11, 2015 for U.S. Appl. No. 13/462,004.
Raoul et al., 'Hepatic Artery Injection of I-131-Labeled Lipiodol: Part I: Biodistribution Study Results in Patients with Hepatocellular Carcinoma and Liver Metastases', Radiololgy 168(2): 541-545, Aug. 1988.
Raoul et al., 'Chemoembolization of Hepatocellular Carcinomas. A Study fo the Biodistribution and Pharmacokinetics of Doxorubicin', Cancer 70(3): 585-590, Aug. 1992.
de Baere et al., Quantification of Tumor Uptake of Iodized Oils and Emulsions of Iodized Oils: Experimental Study, Radiology 201: 713-735, 1996.
Hong et al., 'Effects fo the Type of Embolization Particles on Carboplatin Concentration in Liver Tumors After Transcatheter Arterial Chemoembolization in a Rabbit Model of Liver Cancer', J Vasc Interv Radiol 16(12): 1711-1717, 2005.
Namur et al., 'MR Imaging Detection of Superparamagnetic Iron Oxide-Loaded Tris-Acryl Embolization Microspheres', J Vasc Interv Radiol, 18(10): 1287-95, Oct. 2007.
D'Souza et al., 'Methods to Assiss In Vitro Drug Release from Injectable Polymeric Particulate Systems', Pharmaceutical Research, 23(3): 460-74, Mar. 2006.
Kotanski et al., 'A Novel In Vitro Release Technique for Peptide-Containing Biodegradable Microspheres', AAPS PharSciTech, Article 4, 2000.
Haacke et al., 'Susceptibility Weighted Imaging (SWI)', Magnetic Resonance in Medicine 52(3): 612-618, 2004.
Haacke et al., 'Characterizing Iron Deposition in Multiple Sclerosis Lesions Using Susceptibility Weighted Imaging', 29(3): 537-544, 2009.
Namur et al., 'Tissular Distribution and Concentration of Doxorubicin in Pig Liver After Embolization with Drug Eluting Beads', Society fo Interventional Radiology, SIR Washington, Mar. 2008.
Namur et al, 'Diffusion of doxorubicin from Drugs Eluting Beads and Tissular Changes After Embolization in Hepatocellular Carcinoma', Society of Interventional Radiology—SIR San Diego, CA, JVIR book of Abstracts, p. S61, Mar. 2009.

(Continued)

*Primary Examiner* — Michael G. Hartley
*Assistant Examiner* — Leah H Schlientz
(74) *Attorney, Agent, or Firm* — Stoel Rives LLP

(57) ABSTRACT

Biomaterials suitable for use as drug eluting, Magnetic Resonance Imaging ("MRI") detectable implants for vascular occlusion are provided, as are methods of producing such biomaterials. Further, methods of treating an individual suffering from a solid tumor are provided.

20 Claims, 14 Drawing Sheets

(56) References Cited

OTHER PUBLICATIONS

Lee et al., 'Distribution of Iron Oxide-Containing Embosphere Particles After Transcatheter Arterial Embolization in an Animal Model of Liver Cancer: Evaluation with MR Imaging and Implication for Therapy', J Vasc Interv Radiol, 19(10): 1490-1496, Oct. 2008.
International Search Report and Written Opinion dated Aug. 23, 2013 for PCT/US2013/042363.
Laurent, 'Microspheres and Nonspherical Particles for Embolization,' Techniques in Vascular and Interventional Radiology, vol. 10, pp. 248-256, 2007.
Office Action dated Nov. 18, 2013 for U.S. Appl. No. 13/462,004.
Hori et al., 'Study on the Effect of Arterial Embolism with Super-Absorbent Polymer', Intervent Radiology, vol. 11, No. 3, 1996.

\* cited by examiner

# BIOMATERIALS SUITABLE FOR USE AS DRUG ELUTING, MAGNETIC RESONANCE IMAGING DETECTABLE IMPLANTS FOR VASCULAR OCCLUSION

RELATED APPLICATIONS

This application claims priority to U.S. Provisional Application No. 61/651,389 filed on May 24, 2012, titled Biomaterials Suitable for Use as Drug Eluting, Magnetic Resonance Imaging Detectable Implants for Vascular Occlusion, which is hereby incorporated by reference in its entirety.

TECHNICAL FIELD

The present disclosure relates to biomaterials suitable for use as a drug eluting, Magnetic Resonance Imaging ("MRI") detectable implants for vascular occlusion, as well as methods of producing such biomaterials. Further, the disclosure relates to methods of treating an individual suffering from a solid tumor.

BRIEF DESCRIPTION OF THE DRAWINGS

FIG. 5 is a depiction of a generalized dialysis membrane experiment to test drug release from a biomaterial.

DETAILED DESCRIPTION OF CERTAIN EMBODIMENTS

Figure 1:
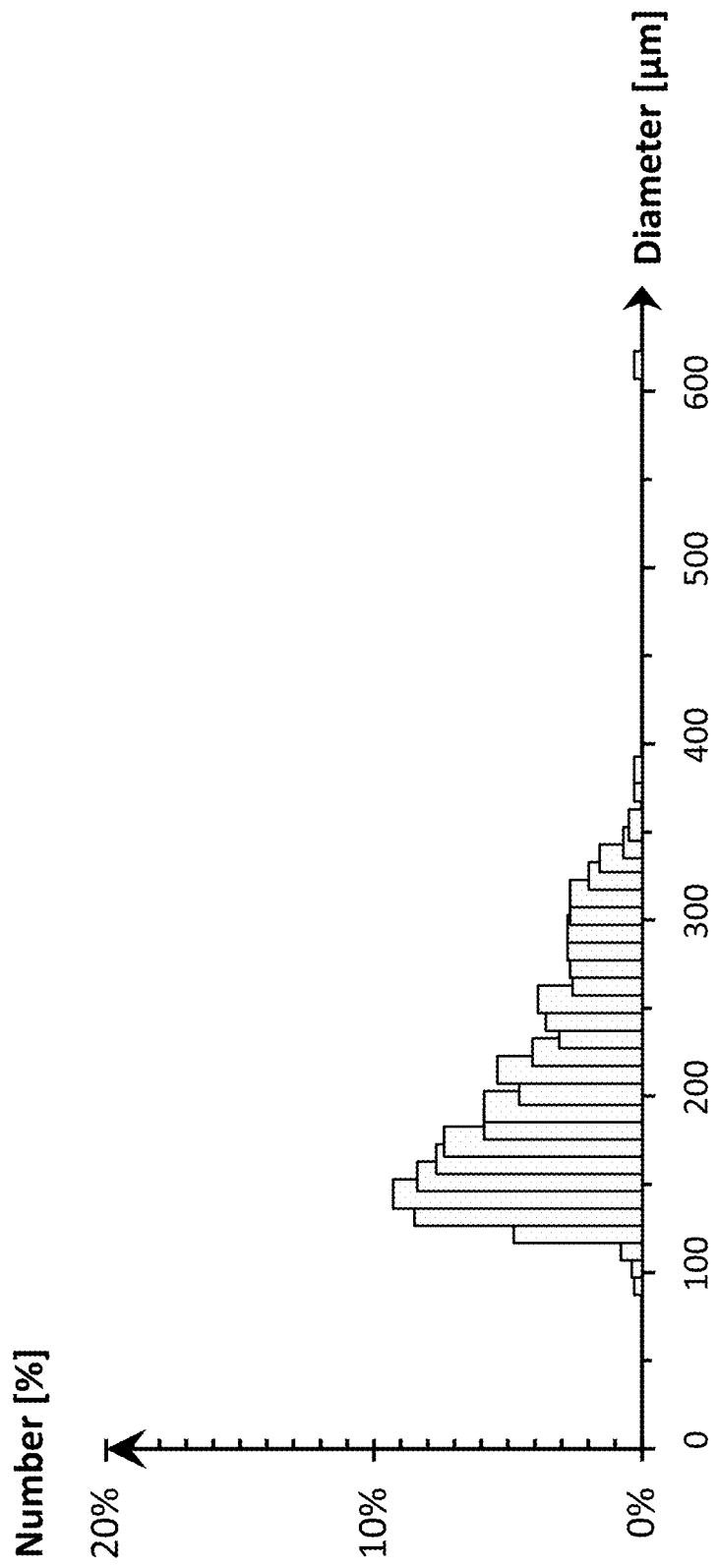
FIG. 1 is a histogram showing the size distribution of microspheres from Example 1.

The present disclosure relates to drug eluting, Magnetic Resonance Imaging ("MRI") detectable implants for vascular occlusion, as well as methods of producing such biomaterials. Further, the disclosure relates to methods of treating an individual suffering from a solid tumor.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

In a first aspect, the present disclosure is related to biomaterials suitable for use as a drug eluting, Magnetic Resonance Imaging ("MRI") detectable implant for vascular occlusion.

In one embodiment, the biomaterial comprises: a polymer comprising at least one of acrylate or vinyl sulfonate; an iron oxide particle; and a drug. In an embodiment, the drug is a chemotherapeutic drug.

In another embodiment, the biomaterial is in the form of a microsphere. In a related embodiment, the microsphere is substantially spherical. In another related embodiment, the microsphere has a major axis of from about 15 micrometers to about 1000 micrometers. In another embodiment, the microsphere has a major axis of from about 100 micrometers to about 300 micrometers.

In another embodiment, the biomaterial comprises a copolymer. In a related embodiment, the copolymer comprises an acrylate, such as sodium acrylate, and an acrylamide. In one embodiment, the copolymer comprises at least one of: sodium acrylate, vinyl sulfonate, AMPS or CEA; and an acrylamide. In a related embodiment, the copolymer comprises: at least one of: sodium acrylate, vinyl sulfonate, AMPS or CEA; and N-[tris-(hydroxymethyl)methyl]acrylamide.

In another embodiment, the polymer comprises a crosslinking agent. In a related embodiment, the crosslinking agent is N,N-methylene-bis-acrylamide.

In one embodiment, the biomaterial comprises: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide.

In a related embodiment, the biomaterial comprises: 5 wt % to 50 wt % sodium acrylate; 0.01 wt % to 10 wt % iron oxide; 10 wt % to 50 wt % N-[tris-(hydroxymethyl)methyl] acrylamide; and 1 wt % to 30 wt % N,N-methylene-bis-acrylamide. In an embodiment, the biomaterial comprises: 5 wt % to 50 wt % vinyl sulfonate; 0.01 wt % to 10 wt % iron oxide; 10 wt % to 50 wt % N-[tris-(hydroxymethyl)methyl] acrylamide; and 1 wt % to 30 wt % N,N-methylene-bis-acrylamide. In an additional embodiment, the biomaterial comprises: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl] acrylamide; and 1 wt % to 30 wt % N,N-methylene-bis-acrylamide. In a further embodiment, the biomaterial comprises: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide.

In an embodiment, the drug is a chemotherapeutic drug. In one embodiment, the drug is irinotecan. In one embodiment, the drug is doxorubicin. In one embodiment, a chemotherapeutic drug is releasably associated with a microsphere. In one embodiment, doxorubicin is releasably associated with a microsphere. In one embodiment, irinotecan is releasably associated with a microsphere. In a related embodiment, a drug is added to a suspension of microspheres in an amount of between about 0.5 mg to about 50 mg per milliliter of the suspension.

In an embodiment, the drug may be a charged drug, or a drug that is charged within the range of physiological pH values, including the pH values in and near tumors. In an embodiment, the drug is a cationic drug. The biomaterial may comprise a polymer which is also charged, by for example, containing ionic groups. In an embodiment, the biomaterial contains anionic groups. In one embodiment, the association of a drug to the biomaterial comprises an ionic interaction.

In one embodiment, the iron oxide is $Fe_3O_4$. In one embodiment, the iron oxide is a mixture of both iron(II) oxide and iron(III) oxide. In one embodiment, the iron oxide particle is a nanoparticle. In a related embodiment, the iron oxide nanoparticle is superparamagnetic. In an embodiment, the iron oxide is in a colloidal form.

In a second aspect, the present disclosure is related to methods of producing a biomaterial suitable for use as a drug eluting, MRI detectable implant for vascular occlusion.

In one embodiment, the method comprises providing a polymer comprising at least one of an acrylate, vinyl sulfonate, AMPS or CEA, wherein the polymer is associated with an iron oxide particle; and associating the polymer with a chemotherapeutic drug. In an embodiment, the acrylate is sodium acrylate.

In one embodiment, providing the polymer comprises polymerizing a monomer composition in the presence of an iron oxide particle, wherein the monomer composition comprises at least one of an acrylate such as sodium acrylate, vinyl sulfonate, AMPS or CEA. In another embodiment, providing the polymer comprises polymerizing a monomer composition in the presence of an iron oxide particle, wherein the monomer composition comprises: at least one of sodium acrylate, vinyl sulfonate, AMPS or CEA; and one other monomer. In another embodiment, providing the polymer comprises polymerizing a monomer composition in the presence of an iron oxide particle, wherein the monomer composition comprises: at least one of sodium acrylate, vinyl sulfonate, AMPS or CEA; and N-[tris-(hydroxymethyl)methyl]acrylamide. In another embodiment, providing the polymer comprises polymerizing a monomer composition in the presence of an iron oxide particle, wherein the monomer composition comprises: at least one of sodium acrylate, vinyl sulfonate, AMPS or CEA; N-[tris-(hydroxymethyl)methyl]acrylamide; and a crosslinking agent. In another embodiment, providing the polymer comprises polymerizing a monomer composition in the presence of an iron oxide particle, wherein the monomer composition comprises: at least one of sodium acrylate, vinyl sulfonate, AMPS or CEA; N-[tris-(hydroxymethyl)methyl]acrylamide; and N,N-methylene-bis-acrylamide.

In one embodiment, providing the polymer comprises providing a mixture comprising: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide; and polymerizing the mixture.

In a related embodiment, providing the polymer comprises providing a mixture comprising: 5 wt % to 50 wt % sodium acrylate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In an embodiment, providing the polymer comprises providing a mixture comprising: 5 wt % to 50 wt % vinyl sulfonate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In an additional embodiment, providing the polymer comprises providing a mixture comprising: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In a further embodiment, providing the polymer comprises providing a mixture comprising: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture.

In one embodiment, the monomer composition and the iron oxide particle are mixed to form a mixture before polymerizing the monomer composition in the presence of the iron oxide particle. In a related embodiment, the method further comprises heating the mixture before polymerizing the monomer composition in the presence of the iron oxide particle. In a related embodiment, heating the mixture comprises heating the mixture to a temperature of from about 20° C. to about 80° C. In a related embodiment, heating the mixture comprises heating the mixture to about 50° C.

In another embodiment, polymerizing the monomer composition in the presence of the iron oxide particle further comprises forming a polymeric microsphere associated with an iron oxide particle. In a related embodiment, polymerizing the monomer composition in the presence of the iron oxide particle takes place in oil, such that a polymeric microsphere associated with an iron oxide particle is formed. In a related embodiment, the oil is at a temperature of from about 30° C. to about 100° C. In a related embodiment, the oil is at a temperature of about 60° C. In a related embodiment, the polymeric microspheres are sieved to obtain polymeric microspheres with a major axis of from about 15 micrometers to about 1000 micrometers. In a related embodiment, the polymeric microspheres are sieved to obtain polymeric microspheres with a major axis of from about 100 micrometers to about 300 micrometers.

In one embodiment, the iron oxide is $Fe_3O_4$. In one embodiment, the iron oxide particle is a nanoparticle. In a related embodiment, the iron oxide nanoparticle is superparamagnetic.

In one embodiment, the chemotherapeutic drug is doxorubicin. In one embodiment, the chemotherapeutic drug is irinotecan.

In one embodiment, the polymer is in the form of a microsphere.

In one embodiment, the method further comprises: suspending the microsphere in a liquid and adding a drug to the suspension in an amount of between about 0.5 mg to about 50 mg per milliliter of the suspension.

In a third aspect, the present disclosure is related to methods of treating an individual suffering from a solid tumor comprising: administering to the individual a drug eluting, MRI detectable implant for vascular occlusion, comprising: a polymer comprising at least one of an acrylate, such as sodium acrylate, vinyl sulfonate, AMPS or CEA; an iron oxide particle; and a chemotherapeutic drug, wherein administering to the individual the drug eluting, MRI detectable implant for vascular occlusion leads to occlusion of a blood vessel associated with the solid tumor and delivery of the chemotherapeutic agent to the solid tumor.

In one embodiment, the method further comprises identifying the location of the drug eluting, MRI detectable implant for vascular occlusion through MRI after administering to the individual the drug eluting, MRI detectable implant for vascular occlusion.

In one embodiment, the drug eluting, MRI detectable implant for vascular occlusion is in the form of one or more microspheres. In a related embodiment, administering to the individual the drug eluting, MRI detectable implant for vascular occlusion comprises introducing the one or more microspheres into the lumen of a blood vessel associated with the solid tumor through a catheter. In another related embodiment, the drug eluting, MRI detectable implant for vascular occlusion is suspended in a liquid and a drug is added to the suspension of the drug eluting, MRI detectable implant in an amount of between about 0.5 mg to about 50 mg per milliliter of the suspension.

In one embodiment, the polymer comprises a copolymer. In a related embodiment, the copolymer comprises: at least one of an acrylate, such as sodium acrylate, vinyl sulfonate, AMPS or CEA; and N-[tris-(hydroxymethyl)methyl]acrylamide. In another embodiment, the copolymer comprises: at least one of sodium acrylate, vinyl sulfonate, AMPS or CEA; N-[tris-(hydroxymethyl)methyl]acrylamide; and N,N-methylene-bis-acrylamide.

In one embodiment, the drug eluting, MRI detectable implant for vascular occlusion comprises: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide.

In a related embodiment, the drug eluting, MRI detectable implant for vascular occlusion comprises: 5 wt % to 50 wt % sodium acrylate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an embodiment, the drug eluting, MRI detectable implant for vascular occlusion comprises: 5 wt % to 50 wt % vinyl sulfonate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an additional embodiment, the drug eluting, MRI detectable implant for vascular occlusion comprises: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In a further embodiment, the drug eluting, MRI detectable implant for vascular occlusion comprises: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide.

In one embodiment, the iron oxide is $Fe_3O_4$. In one embodiment, the iron oxide particle is a nanoparticle. In a related embodiment, the iron oxide nanoparticle is superparamagnetic. In an embodiment, the iron oxide is in a colloidal form.

Definitions

Unless specifically defined otherwise, technical terms, as used herein, have their normal meaning as understood in the art. The following terms are specifically defined with examples for the sake of clarity.

A "biomaterial" means any composition that is suitable for introducing into the body of an individual.

A "microsphere" means a composition having a generally ellipsoid shape and a major axis in the size range of from about 15 μm to about 1000 μm. In some embodiments, the microsphere will have a spheroid shape, in other embodiments, the microsphere will have a spherical shape. In other embodiments, the microsphere will be substantially spherical.

In the context of a microsphere, "major axis" means the longest axis that can be drawn through the ellipsoid shape of the microsphere.

In the context of a microsphere, "minor axis" means the shortest axis that may be drawn through the ellipsoid shape of the microsphere perpendicular to the major axis.

In the context of a microsphere, "substantially spherical" means that the length of the minor axis of the microsphere is at least 80% of the length of the major axis of the microsphere. In some embodiments, the length of the minor axis of the microsphere is at least 85% of the length of the major axis of the microsphere. In some embodiments, the length of the minor axis of the microsphere is at least 90% of the length of the major axis of the microsphere. In some embodiments, the length of the minor axis of the microsphere is at least 95% of the length of the major axis of the microsphere. In some embodiments, the length of the minor axis of the microsphere is at least 99% of the length of the major axis of the microsphere.

In some embodiments, the microsphere will appear smooth at up to 1000× (times) magnification, (i.e., the surface of the microsphere does not include an irregularity which would cause the minor axis to be less than 95% of the length of the major axis). In another embodiment, the microspheres do not have irregularities on the surface. In another embodiment, the microspheres do not have indentations on the surface.

In the context of a polymer, a polymer "comprises" a monomer if the polymer has at least one of the monomer covalently bound to the polymer (i.e., a polymerized monomer).

A "monomer composition" means any composition comprising at least one monomer that may be polymerized to form a polymer. The monomer composition may optionally comprise other components besides the at least one monomer. For example, the monomer composition may comprise additional agents to aid in the polymerization process, or it may comprise non-monomer compositions that should be incorporated or associated with the final polymer after polymerization.

"Polymerize" or "polymerizing" means any action taken to cause one or more monomers to become covalently bound to a polymer. For example, a monomer composition or mixture may be polymerized by adding an activating agent to the monomer composition or mixture to induce formation of a polymer. In some embodiments, the activating agent comprises N,N,N',N'-tetramethylethylenediamine ("TEMED").

A compound is "incorporated into" a composition when the compound is covalently or non-covalently bound to the composition, such that in at least some conditions, the compound will not be released from the composition. For example a compound, such as iron oxide, may be incorporated into a composition, such as a polymer, so that when the polymer is introduced into an individual, at least a portion of the iron oxide will remain bound to the polymer.

A compound is "releasably associated" with a composition when the compound is covalently or non covalently bound to the composition such that in at least some conditions, the compound will not remain bound to the composition. For example, a compound, such as a drug, may be releasably bound to a composition, such as a microsphere, so that when the microsphere is introduced into an individual, at least a portion of the drug will not remain bound to the microsphere.

Biomaterials

In a first aspect, the present disclosure is related to biomaterials suitable for use as a drug eluting, Magnetic Resonance Imaging ("MRI") detectable implant for vascular occlusion.

In some embodiments, the biomaterial comprises a polymer. In some embodiments, the polymer comprises an acrylate, such as sodium acetate. In some embodiments, the polymer comprises at least one of sodium acrylate, vinyl sulfonate, AMPS or CEA. When reciting that a polymer comprises an acrylate, vinyl sulfonate or some other monomer, it is understood to mean that the polymer comprises a polymerized form of such monomer.

In another embodiment, the polymer is a copolymer. In some embodiments, the copolymer comprises an acrylate, such as sodium acrylate, and another monomer. In some embodiments, the copolymer comprises at least one of sodium acrylate, vinyl sulfonate, AMPS or CEA, and another monomer. In some embodiments, the additional monomer comprises an acrylamide, such as N-[tris-(hydroxymethyl)methyl]acrylamide.

In another embodiment, the polymer further comprises a crosslinking agent. In some embodiments, the crosslinking agent comprises N,N-methylene-bis-acrylamide. In other embodiments, the crosslinking agent may comprise 1-(acryloyloxy)-3-(methacryloyloxy)-2-propanol, 1,4-diacryloylpiperazine, diethylene glycol diacrylate, ethylene glycol dimethacrylate, piperazine diacrylate, N,N'-bisacrylylcystamide, or N,N'-diallyl tartardiamide.

In some embodiments, the polymer comprises an acrylate, N-[tris-(hydroxymethyl)methyl]acrylamide, and N,N-methylene-bis-acrylamide. In other embodiments, the polymer comprises sodium acrylate, N-[tris-(hydroxymethyl)methyl]acrylamide, and N,N-methylene-bis-acrylamide. In other embodiments, the polymer comprises vinyl sulfonate, N-[tris-(hydroxymethyl)methyl]acrylamide, and N,N-methylene-bis-acrylamide. In other embodiments, the polymer comprises AMPS, N-[tris-(hydroxymethyl)methyl]acrylamide, and N,N-methylene-bis-acrylamide. In other embodiments, the polymer comprises CEA, N-[tris-(hydroxymethyl)methyl]acrylamide, and N,N-methylene-bis-acrylamide. In other embodiments, the polymer comprises at least one of sodium acrylate, vinyl sulfonate, AMPS or CEA, N-[tris-(hydroxymethyl)methyl]acrylamide, and N,N-methylene-bis-acrylamide.

In some embodiments, the biomaterial comprises an iron oxide particle. In some embodiments, the biomaterial comprises $Fe_3O_4$. In some embodiments, the biomaterial comprises an iron oxide nanoparticle. In some embodiments, the biomaterial comprises a superparamagnetic iron oxide particle. In some embodiments, the superparamagnetic iron oxide particle is an iron oxide nanoparticle. In an embodiment, the iron oxide is in a colloidal form. In some embodiments, the iron oxide particle is associated with the polymer. In some embodiments, the iron oxide particle is incorporated into the polymer.

In some embodiments, the biomaterial comprises: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide.

In a related embodiment, the biomaterial comprises: 5 wt % to 50 wt % sodium acrylate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an embodiment, the biomaterial comprises: 5 wt % to 50 wt % vinyl sulfonate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an additional embodiment, the biomaterial comprises: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In a further embodiment, the biomaterial comprises: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide.

In some embodiments, the biomaterial is formed so that it is in an appropriate shape to occlude a blood vessel. In some embodiments, the biomaterial is in the form of a microparticle. In some embodiments, the biomaterial is in the form of a microsphere. In other embodiments, the microsphere is substantially spherical. In some embodiments, the microspheres may have an average major axis of from about 15 micrometers to about 1000 micrometers. In some embodiments, the microspheres may have an average major axis of from about 100 micrometers to about 800 micrometers. In some embodiments, the microspheres may have an average major axis of from about 200 micrometers to about 600 micrometers. In some embodiments, the microspheres may have an average major axis of from about 100 micrometers to about 300 micrometers. In some embodiments, the microspheres may have an average major axis of from about 50 micrometers to about 150 micrometers. In certain embodiments, the microspheres may have an average major axis of from about 50 micrometers to about 100 micrometers. In some embodiments, the microspheres may have an average major axis of from about 30 micrometers to about 100 micrometers.

In some embodiments, the biomaterial comprises a drug. In some embodiments, the drug is releasably associated with the biomaterial. In some embodiments, the drug is releasably associated to a microsphere. In some embodiments, the drug is doxorubicin. In some embodiments, the drug is irinotecan. In some embodiments, the biomaterial is suspended in a liquid and a drug is added to a suspension of microspheres in an amount of between about 0.5 mg to about 50 mg per milliliter of the suspension.

Methods of Producing Biomaterials

In a second aspect, the present disclosure is related to methods of producing a biomaterial suitable for use as a drug eluting, MRI detectable implant for vascular occlusion.

In some embodiments, the method comprises providing a polymer associated with an iron oxide particle, and associating the polymer with a drug. In an embodiment, the drug is a chemotherapeutic drug.

The polymer associated with an iron oxide polymer may be provided in various ways. For example, the polymer may be sourced from a third party, or it may be generated prior to associating the polymer with the drug.

In some embodiments, providing the polymer comprises polymerizing a monomer composition in the presence of an iron oxide particle. The monomer composition may be polymerized according using an appropriate activating agent. For example, an amide may be used as an activating agent. In an embodiment, N,N,N',N'-tetramethylethylenediamine ("TEMED") may be used as an activating agent. In an embodiment, triethyl amine may be used as an activating agent.

In some embodiments, the monomer composition comprises acrylate, such as sodium acrylate. In some embodiments, the monomer composition comprises vinyl sulfonate. In some embodiments, the monomer composition comprises AMPS. In certain embodiments, the monomer composition comprises at least one of sodium acrylate, vinyl sulfonate, AMPS or CEA.

In some embodiments, the monomer composition comprises acrylate and an additional monomer. In some embodiments, the monomer composition comprises vinyl sulfonate and an additional monomer. In some embodiments, the monomer composition comprises AMPS and an additional monomer. In some embodiments, the monomer composition comprises at least one of sodium acrylate, vinyl sulfonate, AMPS or CEA, and an additional monomer.

In some embodiments, the monomer composition comprises acrylate and an acrylamide, such as N-[tris-(hydroxymethyl)methyl]acrylamide. In some embodiments, the monomer composition comprises sodium acrylate and an acrylamide. In some embodiments, the monomer composition comprises vinyl sulfonate and an acrylamide, such as N-[tris-(hydroxymethyl)methyl]acrylamide. In some embodiments, the monomer composition comprises AMPS and an acrylamide. In some embodiments, the monomer composition comprises at least one of sodium acrylate, vinyl sulfonate, AMPS or CEA, and N-[tris-(hydroxymethyl)methyl]acrylamide.

In some embodiments, the monomer composition comprises acrylate, such as sodium acrylate, and a crosslinking agent. In some embodiments, the monomer composition comprises vinyl sulfonate and a crosslinking agent. In some embodiments, the monomer composition comprises AMPS and a crosslinking agent. In some embodiments, the monomer composition comprises at least one of sodium acrylate, vinyl sulfonate, AMPS or CEA, and a crosslinking agent.

In some embodiments, the monomer composition comprises acrylate and N,N-methylene-bis-acrylamide. In some embodiments, the monomer composition comprises sodium acrylate and N,N-methylene-bis-acrylamide. In some embodiments, the monomer composition comprises vinyl sulfonate and N,N-methylene-bis-acrylamide. In some embodiments, the monomer composition comprises AMPS and N,N-methylene-bis-acrylamide. In some embodiments, the monomer composition comprises at least one of sodium acrylate, vinyl sulfonate, AMPS or CEA, and N,N-methylene-bis-acrylamide.

In some embodiments, the monomer composition comprises acrylate, an additional monomer and a crosslinking agent. In some embodiments, the monomer composition comprises sodium acrylate, an additional monomer and a crosslinking agent. In some embodiments, the monomer composition comprises vinyl sulfonate, an additional monomer and a crosslinking agent. In some embodiments, the monomer composition comprises AMPS, an additional monomer and a crosslinking agent. In some embodiments, the monomer composition comprises at least one of sodium acrylate, vinyl sulfonate, AMPS or CEA, an additional monomer and a crosslinking agent.

In some embodiments, the monomer composition comprises acrylate, N-[tris-(hydroxymethyl)methyl]acrylamide and N,N-methylene-bis-acrylamide. In some embodiments, the monomer composition comprises sodium acrylate, N-[tris-(hydroxymethyl)methyl]acrylamide and N,N-methylene-bis-acrylamide. In some embodiments, the monomer composition comprises vinyl sulfonate, N-[tris-(hydroxymethyl)methyl]acrylamide and N,N-methylene-bis-acrylamide. In some embodiments, the monomer composition comprises AMPS, N-[tris-(hydroxymethyl)methyl]acrylamide and N,N-methylene-bis-acrylamide. In some embodiments, the monomer composition comprises at least one of sodium acrylate, vinyl sulfonate, AMPS or CEA, N-[tris-(hydroxymethyl)methyl]acrylamide and N,N-methylene-bis-acrylamide.

In some embodiments, the monomer composition is polymerized in the presence of an iron oxide nanoparticle. In an embodiment, the monomer composition is polymerized in the presence of colloidal iron oxide. In some embodiments, the monomer composition is polymerized in the presence of $Fe_3O_4$. In some embodiments, the monomer composition is polymerized in the presence of a superparamagnetic iron oxide particle. In some embodiments, the monomer composition is polymerized in the presence of the iron oxide particle such that the iron oxide particle is incorporated into the resulting polymer.

In some embodiments, the monomer composition and the iron oxide particle are mixed to form a mixture before polymerizing the monomer composition. In some embodiments, the mixture is heated, before polymerizing the monomer composition. The mixture may be heated to a temperature of from about 20° C. to about 100° C. In one embodiment, the mixture is heated to from about 30° C. to about 80° C. In an embodiment, the mixture is heated to about 50° C.

In some embodiments, obtaining the polymer comprises providing a mixture comprising: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide; and polymerizing the mixture.

In a related embodiment, obtaining the polymer comprises providing a mixture comprising: 5 wt % to 50 wt % sodium acrylate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In an embodiment, obtaining the polymer comprises providing a mixture comprising: 5 wt % to 50 wt % vinyl sulfonate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In an additional embodiment, obtaining the polymer comprises providing a mixture comprising: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture. In a further embodiment, obtaining the polymer comprises providing a mixture comprising: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide; and polymerizing the mixture.

In some embodiments, additional agents may be added to the monomer composition or mixture prior to polymerization. For example in some embodiments, one or more salts are added. In another embodiment, one or more buffers are added. In some embodiments, at least one of sodium chloride, sodium acetate or glycerol are added. In some embodiments, the pH is adjusted prior to polymerization. In some embodiments, the pH is adjusted to a range of from about 2 to about 10 prior to polymerization. In some embodiments, the pH is adjusted to between 5.9 and 6.1.

In some embodiments, polymerizing the monomer composition or polymerizing the mixture, comprises forming a polymeric microsphere associated with an iron oxide particle. In some embodiments, polymerizing the monomer composition or polymerizing the mixture, comprises adding the monomer composition or the mixture to oil, such that a polymeric microsphere associated with an iron oxide particle is formed. In some embodiments, the oil is paraffin oil. Other oils that may be used include, for example, silicon oil.

In some embodiments, the oil is heated before adding the monomer composition or the mixture to the oil. The oil may be heated to a temperature of from about 20° C. to about 100° C. In one embodiment, the mixture is heated to from about 30° C. to about 80° C. In a related embodiment, the oil is at a temperature of about 60° C.

In some embodiments, after adding the monomer composition or the mixture to the oil, the resulting suspension is stirred. In some embodiments, the speed at which the suspension is stirred will change the distribution of the lengths of the major axis of the microspheres that are formed. In some embodiments, the oil contains a surfactant. In some embodiments, the oil contains sorbitan sesquioleate. In some embodiments, sorbitan sesquioleate is present in the oil in an amount of from about 0.075% v/v to about 0.1% v/v. In some embodiments, sorbitan sesquioleate is present in the oil in an amount of from about 0.01% v/v to about 5% v/v.

In some embodiments, the monomer composition or mixture is allowed to polymerize for between about 15 minutes to about 24 hours. In some embodiments, the monomer composition or mixture is allowed to polymerize for between about 30 minutes to about 90 minutes. In one embodiment, the monomer composition or mixture is allowed to polymerize for about 45 minutes.

In some embodiments, the microspheres are washed after polymerization. In some embodiments, the microspheres are washed in water. In some embodiments, the microspheres are washed in a salt solution. In some embodiments, the salt solution comprises sodium chloride. In some embodiments, the water or solution used to wash the microspheres is at a temperature of from about 20° C. to about 90° C.

In some embodiments, the microspheres may have an average major axis of from about 15 micrometers to about 1000 micrometers. In some embodiments, the microspheres may have an average major axis of from about 100 micrometers to about 800 micrometers. In some embodiments, the microspheres may have an average major axis of from about 200 micrometers to about 600 micrometers. In some embodiments, the microspheres may have an average major axis of from about 100 micrometers to about 300 micrometers.

In some embodiments, a sieve is used to obtain a polymeric microsphere with a desired major axis. In some embodiments, the method comprises sieving the polymeric microsphere to obtain a polymeric microsphere with a major axis as recited previously.

In some embodiments, associating the polymer with the drug comprises releasably associating the drug with the biomaterial. In some embodiments, the drug is doxorubicin. In some embodiments the drug is irinotecan. In some embodiments, the drug is an anti-angiogenic drug. In some embodiments, the drug is a chemotherapeutic drug. In some embodiments, the chemotherapeutic drug is at least one of: doxorubicin, irinotecan and sunitinib. In some embodiments, the chemotherapeutic drug is associated with a polymeric microsphere. In some embodiments, the polymer microsphere is suspended in a liquid and a drug is added to the suspension in an amount of between about 0.5 mg to about 50 mg per milliliter of the suspension.

In some embodiments, contacting the biomaterial with the drug comprises adding the biomaterial to a solution of the drug. In some embodiments, after adding the biomaterial to the solution of the drug, the solution of the drug is agitated. In some embodiments, the solution of the drug contains the drug in an amount of from about 10 mg to about 50 mg. In some embodiments, the biomaterial is incubated with the solution of the drug for a period of from about 15 minutes to about 2 hours. In some embodiments, the biomaterial is incubated with the solution of the drug for a period of at least 15, 30, 45, 60, 90, 120 or 180 minutes.

Methods of Treatment

In a third aspect, the present disclosure is directed to methods of treating an individual suffering from a solid tumor. In one embodiment, the solid tumor is a hepatic tumor.

In one embodiment, the method comprises administering to the individual a drug eluting, MRI detectable implant for vascular occlusion.

In one embodiment, administering to the individual the drug eluting, MRI detectable implant for vascular occlusion leads to occlusion of a blood vessel associated with the solid tumor. In another embodiment, administering to the individual the drug eluting, MRI detectable implant for vascular occlusion leads to delivery of a chemotherapeutic agent to the solid tumor. In one embodiment, administering to the individual the drug eluting, MRI detectable implant for vascular occlusion leads to occlusion of a blood vessel associated with the solid tumor and delivery of a chemotherapeutic agent to the solid tumor.

In one embodiment, the drug eluting, MRI detectable implant for vascular occlusion comprises a polymer. In one embodiment, the drug eluting, MRI detectable implant for vascular occlusion comprises an iron oxide particle. In one embodiment, the drug eluting, MRI detectable implant for vascular occlusion comprises a chemotherapeutic drug.

In one embodiment, the drug-eluting, MRI detectable implant for vascular occlusion comprises, a polymer, an iron oxide particle and a chemotherapeutic drug.

In one embodiment, the polymer comprises acrylate, such as sodium acrylate. In other embodiments, the polymer comprises vinyl sulfonate. In other embodiments, the polymer comprises AMPS. In some embodiments, the polymer comprises at least one of sodium acrylate, vinyl sulfonate, AMPS or CEA.

In another embodiment, the polymer is a copolymer. In some embodiments, the copolymer comprises acrylate, such as sodium acrylate, and another monomer. In some embodiments, the copolymer comprises vinyl sulfonate and another monomer. In some embodiments, the copolymer comprises AMPS and another monomer. In some embodiments, the copolymer comprises at least one of sodium acrylate, vinyl sulfonate, AMPS or CEA, and another monomer. In some embodiment, the additional monomer comprises an acrylamide, such as N-[tris-(hydroxymethyl)methyl]acrylamide.

In another embodiment, the polymer further comprises a crosslinking agent. In some embodiments, the crosslinker comprises N,N-methylene-bis-acrylamide. In other embodiments, the crosslinking agent may comprise 1-(acryloyloxy)-3-(methacryloyloxy)-2-propanol, 1,4-diacryloylpiperazine, diethylene glycol diacrylate, ethylene glycol dimethacrylate, piperazine diacrylate, N,N'-bisacrylylcystamide, or N,N'-diallyl tartardiamide.

In some embodiments, the polymer comprises acrylate, N-[tris-(hydroxymethyl)methyl]acrylamide, and N,N-methylene-bis-acrylamide. In some embodiments, the polymer comprises sodium acrylate, N-[tris-(hydroxymethyl)methyl]acrylamide, and N,N-methylene-bis-acrylamide. In other embodiments, the polymer comprises vinyl sulfonate, N-[tris-(hydroxymethyl)methyl]acrylamide, and N,N-methylene-bis-acrylamide. In other embodiments, the polymer comprises AMPS, N-[tris-(hydroxymethyl)methyl]acrylamide, and N,N-methylene-bis-acrylamide. In other embodiments, the polymer comprises at least one of sodium acrylate, vinyl sulfonate, AMPS or CEA, N-[tris-(hydroxymethyl)methyl]acrylamide, and N,N-methylene-bis-acrylamide.

In some embodiments, the biomaterial comprises an iron oxide particle. In some embodiments, the biomaterial comprises $Fe_3O_4$. In some embodiments, the biomaterial comprises an iron oxide nanoparticle. In some embodiments, the biomaterial comprises a superparamagnetic iron oxide particle. In some embodiments, the superparamagnetic iron oxide particle is an iron oxide nanoparticle. In an embodiment, the biomaterial comprises iron oxide in a colloidal form. In some embodiments, the iron oxide particle is associated with the polymer. In some embodiments, the iron oxide particle is incorporated into the polymer.

In some embodiments, the biomaterial comprises: 0 wt % to 90 wt % sodium acrylate; 0 wt % to 90 wt % vinyl sulfonate; 0 wt % to 90 wt % 2-acrylamido-2-methylpropane sulfonic acid (AMPS); 0 wt % to 90 wt % 2-carboxyethyl acrylate (CEA); 0.01 wt % to 10 wt % iron oxide; 0 wt % to 50 wt % N-[tris-(hydroxymethyl)methyl]acrylamide; and 1 wt % to 30 wt % N,N-methylene-bis-acrylamide.

In a related embodiment, the biomaterial comprises: 5 wt % to 50 wt % sodium acrylate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an embodiment, the biomaterial comprises: 5 wt % to 50 wt % vinyl sulfonate; 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In an additional embodiment, the biomaterial comprises: 5 wt % to 50 wt % 2-acrylamido-2-methylpropane sulfonic acid (AMPS); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide. In a further embodiment, the biomaterial comprises: 5 wt % to 50 wt % 2-carboxyethyl acrylate (CEA); 0.01 wt % to 10 wt % iron oxide; 10 wt % to 50 wt % N-[tris-(hydroxymethyl)methyl]acrylamide; and 1 wt % to 30 wt % N,N-methylene-bis-acrylamide.

In another embodiment, the method further comprises subjecting the individual to MRI. In one embodiment, the individual is subjected to MRI to determine where in the individual the drug eluting, MRI detectable implant for vascular occlusion is located.

In some embodiments, the drug eluting, MRI detectable implant for vascular occlusion is formed so that it is in an appropriate shape to occlude a blood vessel. In some embodiments, the drug eluting, MRI detectable implant for vascular occlusion is in the form of one or more microparticles. In some embodiments, the drug eluting, MRI detectable implant for vascular occlusion is in the form of one or more microspheres. In other embodiments, the one or more microspheres are substantially spherical. In some embodiments, the one or more microspheres have a major axis of from about 15 micrometer to about 1000 micrometers. In some embodiments, the one or more microspheres have a major axis of from about 100 micrometers to about 800 micrometers. In some embodiments, the one or more microspheres have a major axis of from about 200 micrometers to about 600 micrometers. In some embodiments, the one or more microspheres have a major axis of from about 100 micrometers to about 300 micrometers.

In one embodiment, administering to the individual the drug eluting, MRI detectable implant for vascular occlusion comprises introducing the one or more microspheres into the lumen of a blood vessel associated with the solid tumor through a catheter. In one embodiment, when treating an individual with a hepatic tumor, a catheter is inserted via the femoral or brachial artery and advanced into the hepatic artery by steering it through the arterial system under fluoroscopic guidance. Alternatively or in addition, the catheter may be inserted and advanced by steering it through the arterial system under MRI guidance. The catheter is advanced into the hepatic arterial tree as far as necessary to allow complete blockage of the blood vessels supplying the tumor(s), while sparing as many of the arterial branches supplying normal structures as possible. This may be a segmental branch of the hepatic artery, but it could be the entire hepatic artery distal to the origin of the gastroduodenal artery, or even multiple separate arteries. The artery that will need to be blocked depends on the extent of tumor and its individual blood supply. Once the desired catheter position is achieved, the artery is embolized by injecting the therapeutic compositions as described herein through the arterial catheter until flow in the artery to be blocked ceases, for example, after observation for 5 minutes. Occlusion of the artery may be confirmed by subjecting an individual to MRI to determine where in the individual the drug eluting, MRI detectable implant for vascular occlusion is located, and/or injecting radiopaque contrast through the catheter and demonstrating by fluoroscopy or X-ray film that the vessel which previously filled with contrast no longer does so. The same procedure may be repeated with each feeding artery to be occluded.

In some embodiments, the drug eluting, MRI detectable implant for vascular occlusion comprises a chemotherapeutic drug. In some embodiments, the chemotherapeutic drug is releasably associated with the drug eluting, MRI detectable implant for vascular occlusion. In some embodiments, the chemotherapeutic drug is releasably associated to a microsphere. In some embodiments, the chemotherapeutic drug is doxorubicin. In some embodiments, the chemotherapeutic drug is irinotecan. In some embodiments, the biomaterial is suspended in a liquid and a drug is added to the suspension in an amount of between about 0.5 mg to about 50 mg per milliliter of the suspension.

To further illustrate these embodiments, the following examples are provided. These examples are not intended to limit the scope of the claimed invention, which should be determined solely on the basis of the attached claims.

Example 1—Preparation of MRI Detectable Microspheres Using Sodium Acrylate Monomers In a beaker containing 300 ml of demineralized water, 58 g of sodium chloride and 27 g of sodium acetate were dissolved. Next 400 ml of glycerol was added and the pH of the solution was adjusted to between 5.9 and 6.1 with acetic acid. Then, 90 g of N-[tris-(hydroxymethyl)methyl]acrylamide, 19.4 g of sodium acrylate and 10 g of N,N-methylene-bis-acrylamide were added. The volume was adjusted to 1 liter by addition of water and the monomer solution was then heated to 50° C.

Separately, a suspension of 25 ml of iron oxide (ferucarbotran—equivalent to 0.5 mol Fe/L) was filtered. After all monomers were dissolved, the monomer solution was filtered, and the filtered solution of iron oxide was added along with 20 ml of a 70 mg/ml ammonium persulfate solution. This resulting solution was rapidly poured into 4 liters of paraffin oil at 60° C. containing 3 ml of Arlacel 83 (sorbitan sesquioleate) and 4 ml of TEMED (N,N,N',N'-tetramethylethylenediamine) under stirring.

The suspension was left for 45 minutes at 60° C. and the microspheres were then recovered by decanting, and washed with 60° C. water and saline solution to remove the excess oil.

The microspheres were then sieved into different size ranges. The sieved microspheres were then stored in saline. FIG. 1 is a histogram showing the size distribution of microspheres from Example 1. The X axis denotes the size of the microsphere and the Y axis the percentage of microspheres in a given size bin.

Microspheres from Example 1 were subjected to granulometry. As shown, the sieved microspheres formed in Example 1 fall within a particular size distribution of about 200 μm. The results of the granulometry experiments are shown in Table 1.

TABLE 1

Characteristics of MRI Detectable Microspheres from Example 1

|  | Number | Minimum | Maximum | Average |
|---|---|---|---|---|
| Length [μm] | 1259 | 80.18 | 604.83 | 192.41 |
| Width [μm] |  | 75.02 | 590.91 | 188.14 |

Figure 2A:
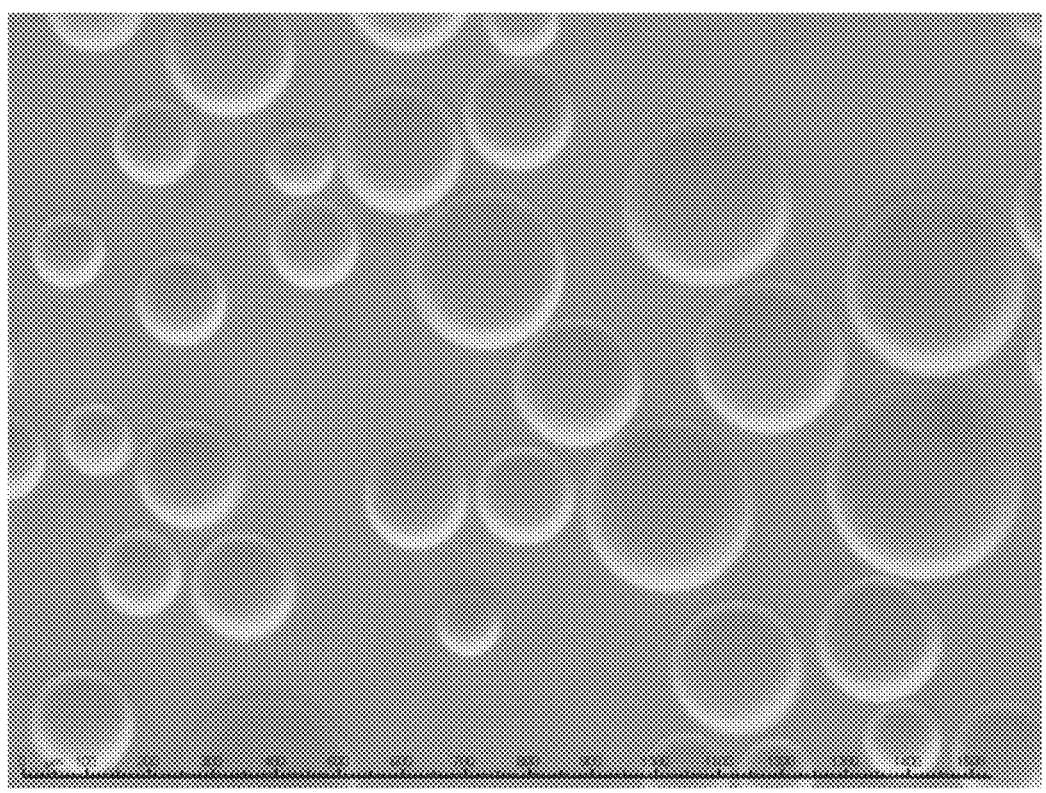
FIGS. 2A and 2B are microscope images of microspheres of Example 1.
Figure 2B:
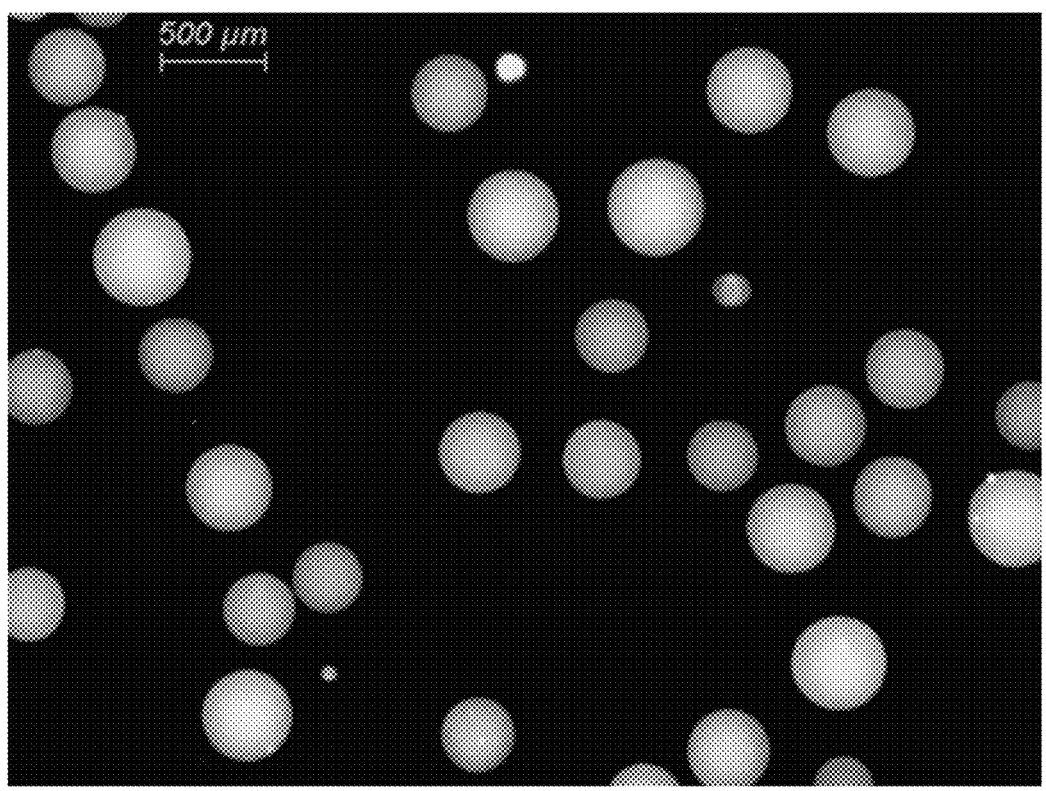

Microspheres from Example 1 were further subjected to microscopy using a microscope linked to a computer for analysis of the images. The microscopy results for Example 1 are shown in FIGS. 2A and 2B. As shown in the images, the microspheres formed in Example 1 are substantially spherical.

Example 2—Preparation of Additional MRI-Detectable Microspheres Using Sodium Acrylate Monomers In a beaker containing 300 ml of demineralized water, 58 g of sodium chloride and 27 g of sodium acetate were dissolved. Next 400 ml of glycerol was added and the pH of the solution was adjusted to between 5.9 and 6.1 with acetic acid. Then, 90 g of N-[tris-(hydroxymethyl)methyl]acrylamide, 70 g of sodium acrylate and 10 g of N,N-methylene-bis-acrylamide were added. The volume was adjusted to 1 liter by addition of water and the monomer solution was then heated to 50° C.

Separately, a suspension of 25 ml of iron oxide (ferucarbotran—equivalent to 0.5 mol Fe/L) was filtered. After all monomers were dissolved, the monomer solution was filtered, and the filtered solution of iron oxide was added along with 20 ml of a 70 mg/ml ammonium persulfate solution. This resulting solution was rapidly poured into 4 liters of paraffin oil at 60° C. containing 3 ml of Arlacel 83 (sorbitan sesquioleate) and 4 ml of TEMED (N,N,N',N'-tetramethylethylenediamine) under stirring.

The suspension was left for 45 minutes at 60° C. and the microspheres were then recovered by decanting, and washed with 60° C. water and saline solution to remove the excess oil.

The microspheres were then sieved into different size ranges. The sieved microspheres were then stored in a solution of equal parts ethanol and water.

Example 3—Drug Loading of MRI Detectable Microspheres of Example 2, Varying the Mass of the Drug Vials containing 2 ml of the microspheres synthesized in Example 2 were washed two times with a saline solution (0.9% NaCl). The excess supernatant was removed and 8 ml of a doxorubicin (Yick Vic lot # IF-DO-071116) solution was added to each vial. Each vial received a solution with a different concentration of doxorubicin such that one vial received 25 mg, one 50 mg, one 75 mg and one 100 mg of doxorubicin. After addition of doxorubicin, the vials were agitated every minute for the first 10 minutes. Samples of 150 μl of supernatant were drawn from each vial at 15, 30, 45, 60, 90, 120 and 180 minutes.

The concentration of doxorubicin in the supernatant was analyzed by reverse phase high performance liquid chromatography (Uptisphere C18 column, 150 mm×4.6 mm). The elution phase consisted in 30% (v/v) acetonitrile and 0.1% (v/v) trifluoroacetic acid in water. UV detection was at $\lambda_{max}$ 480 nm.

The loading efficiency was calculated by using the following equation:

$$\% \text{ loading at time } t = \frac{(\text{initial drug mass}) - (\text{drug mass in the supernatant at time } t)}{\text{initial drug mass}} \times 100$$

with mass at time t=concentration at time t×volume of solution at time t.

Figure 3:
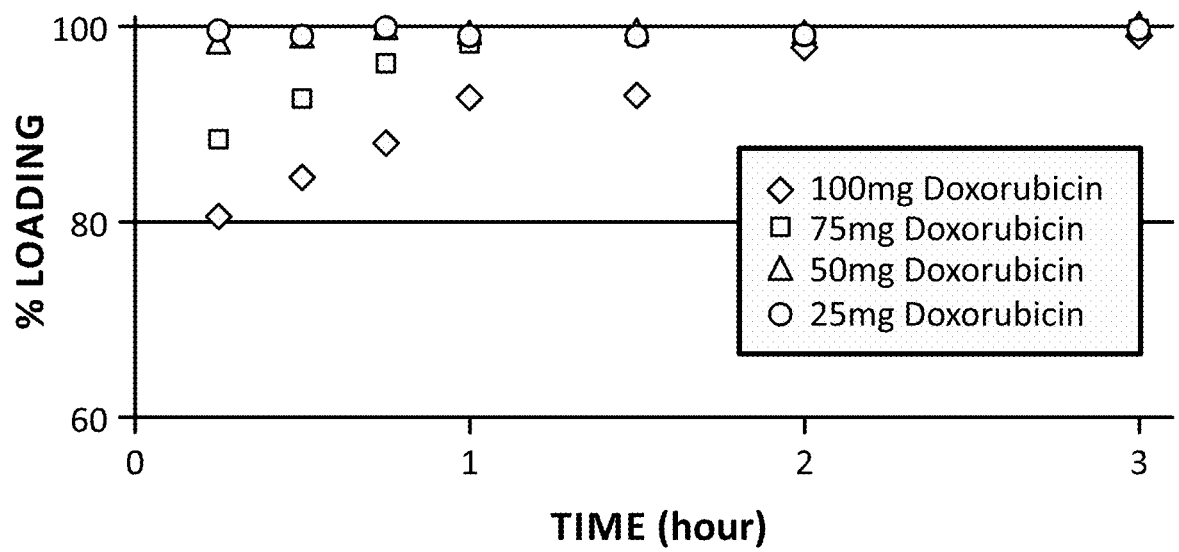
FIG. 3 is a graph depicting the drug loading behavior data collected in Example 3.

The results of the experiment are shown in FIG. 3. The X axis denotes the amount of time the biomaterials were incubated with the doxorubicin solution, and the Y axis denotes the percentage of doxorubicin in the solution that has become associated with the biomaterials. As depicted in the figure, varying amounts of the drug doxorubicin are loaded onto the microspheres in 3 hours or less. Some amounts were loaded in very short times. For example, about 80% loading or greater was achieved in 15 minutes or less.

Example 4—Drug Loading and Release Dynamics for MRI Detectable Microspheres of Example 2, Varying the Mass of the Drug To determine both the loading and release dynamics of the MRI detectable microspheres, microspheres from Example 2 were loaded with 25 or 50 mg of pharmaceutical grade doxorubicin.

In vials containing 2 ml of the microspheres of Example 2, the excess supernatant was removed and 8 ml of a doxorubicin (Adriblastin, Pfizer, lot #8PL007-H) solution was added to each vial. After addition of doxorubicin, the vials were agitated every minute for the first 10 minutes. Samples of 100 μl of supernatant were drawn from each vial at 15, 30, 45, 60, 90 and 120 minutes.

The concentration of doxorubicin in the supernatant was analyzed by reverse phase high performance liquid chromatography (YMC C18 column, 250 mm×4.6 mm). The elution phase consisted in 54% (v/v) water, 29% (v/v) acetonitrile, 17% (v/v) methanol, 2 ml/l phosphoric acid and 1 g/l sodium dodecyl sulfate (pH is adjusted at 3.6). UV detection was at $\lambda_{max}$ 480 nm.

The loading efficiency was calculated using the following equation:

$$\% \text{ loading at time } t = \frac{\text{(initial drug mass)} - \text{(drug mass in the supernatant at time } t)}{\text{initial drug mass}} \times 100$$

with the mass at time t=concentration at time t×volume of solution at time t.

Figure 4:
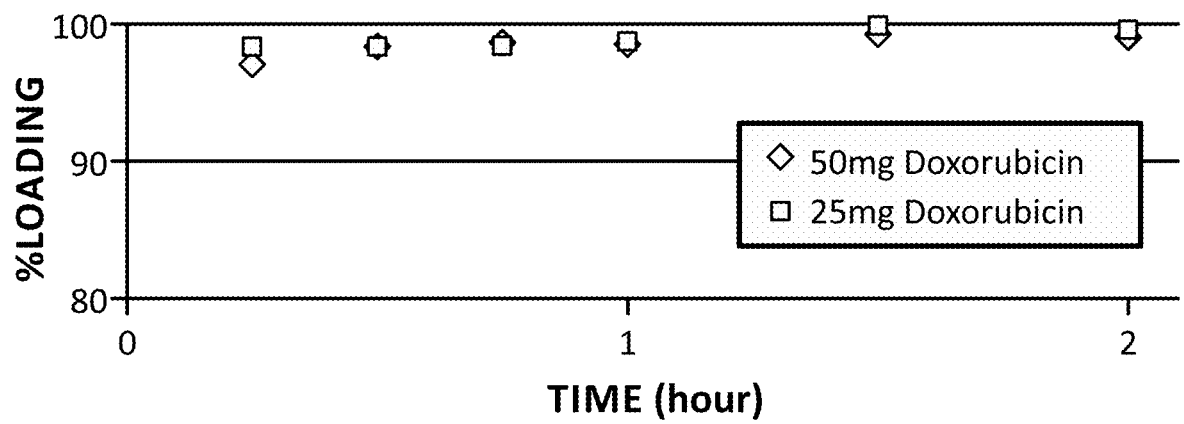
FIG. 4 is a graph depicting the drug release behavior data collected in Example 3.

FIG. 4 shows the loading behavior for this experiment, confirming the data of Example 3. The X axis denotes the amount of time the biomaterials were incubated with the doxorubicin solution, and the Y axis denotes the percentage of doxorubicin in the solution that has become associated with the biomaterials.

A dialysis membrane model was used to analyze the release of doxorubicin from the microspheres over time. Although this model does not simulate the pressure and flow rate from vasculature, for measuring embolization, it is a good model for measuring drug release because the embolic, in vivo, prevents blood flow and the drug release is due to diffusion phenomena.

Figure 5A:
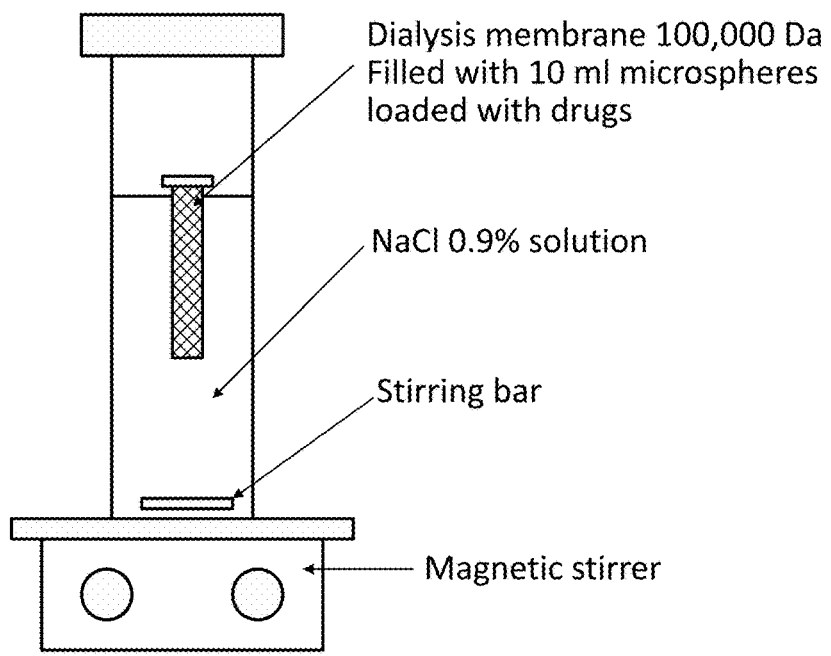
FIG. 5A depicts the apparatus used during dialysis.
Figure 5B:
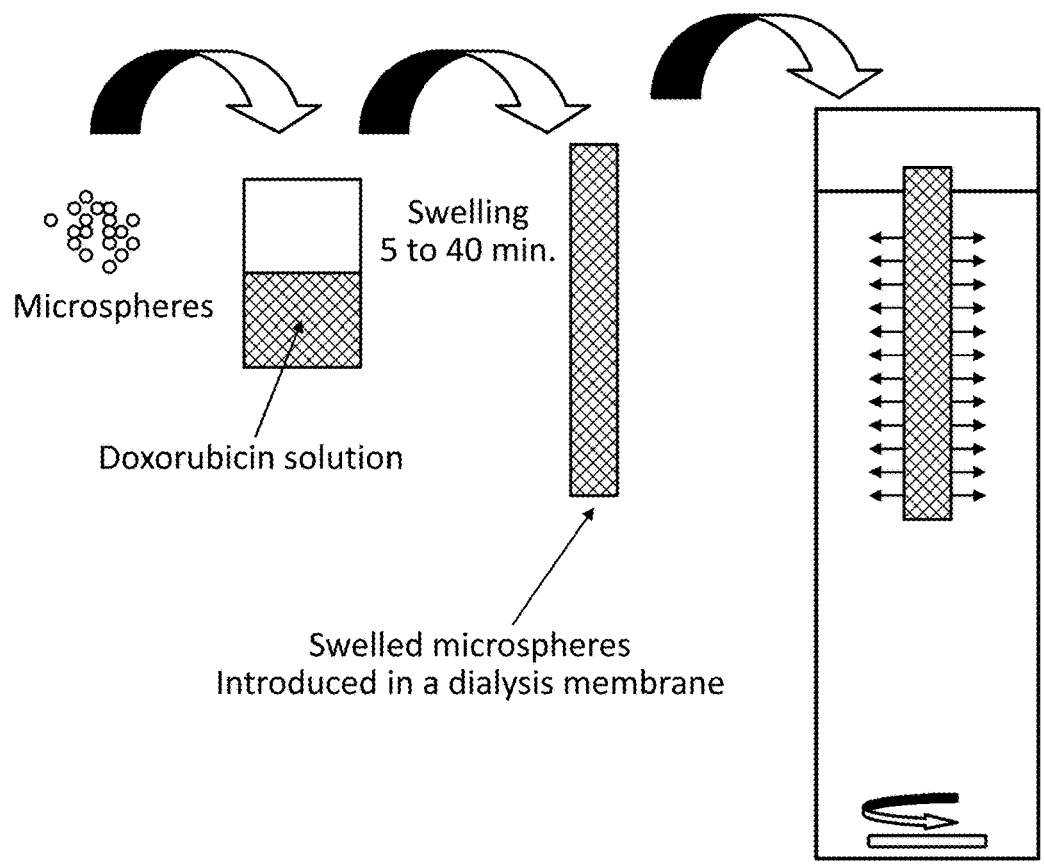
FIG. 5B depicts some of the steps in setting up the dialysis experiment.

Previously obtained results from dialysis experiments assaying the release of peptides from biodegradable microspheres are more predictive of the in vivo onset and duration of release than data obtained from experiments using the extraction method, although the overall in vitro release rate was still somewhat slower than the estimated in vivo release. (See J W Kotanski, P. P. DeLuca, AAPS PharSciTech, 2000, article 4, which is hereby incorporated by reference in its entirety.) The microspheres of the present example were non-degradable microspheres, and the dialysis model was found to be the most appropriate to simulate the release behaviour of implanted microspheres after embolization procedure. FIGS. 5A and 5B show schematics of a typical dialysis membrane model experiment.

Figure 6:
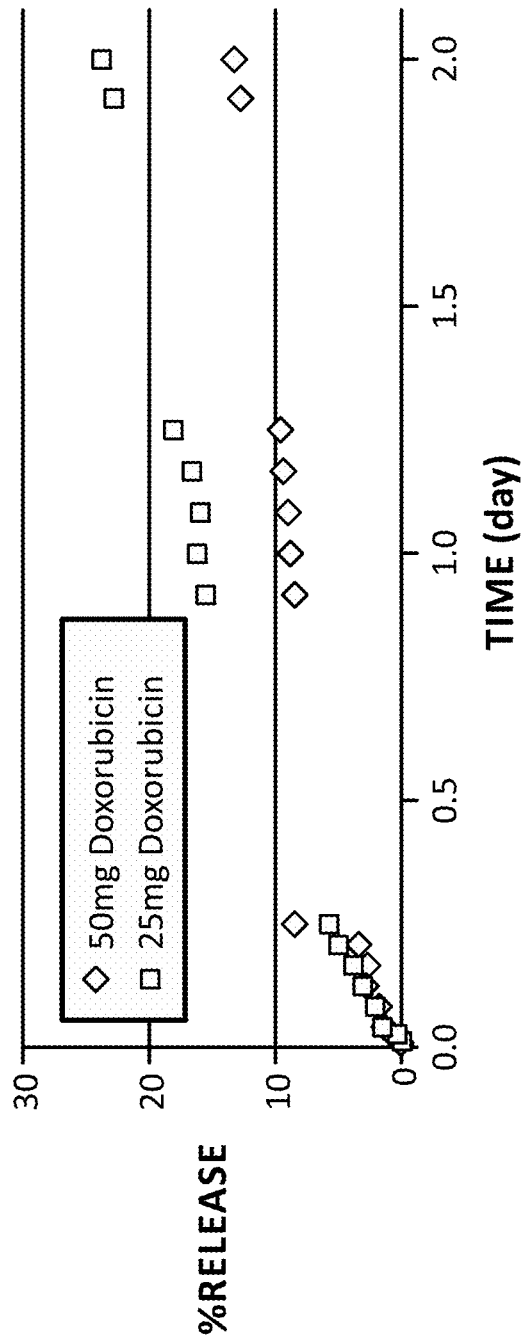
FIG. 6 is a graph depicting the drug release behavior data collected in Example 4.

The study was performed at room temperature. Two ml of drug loaded MRI detectable microspheres from Example 2 were introduced into a 3 ml dialysis membrane (Spectra Por dialysis membrane—MWCO 100,000 Da), which was then introduced in a 250 ml graduated cylinder filled with 250 ml of saline. About 150 μl of the saline solution was sampled periodically from the 250 ml reservoir and the drug content was analysed by HPLC as described in Example 3. The results of the experiment are depicted in FIG. 6. The X axis denotes the amount of time the biomaterial was dialyzed, and the Y axis denotes the percentage of doxorubicin originally associated with the biomaterial that has been released from the from the biomaterial.

Example 5—Preparation of MRI-Detectable Microspheres Using Vinyl Sulfonate Monomers In a beaker containing 300 ml of demineralized water, 58 g of sodium chloride and 27 g of sodium acetate were dissolved. Next 400 ml of glycerol was added and the pH of the solution was adjusted to between 5.9 and 6.1 with acetic acid. Then, 90 g of N-[tris-(hydroxymethyl)methyl]acrylamide, 26.8 g of sodium vinyl sulfonate and 10 g of N,N-methylene-bis-acrylamide were added. The volume was adjusted to 1 liter by addition of water and the monomer solution was then heated to 50° C.

Separately, a suspension of 25 ml of iron oxide (ferucarbotran—equivalent to 0.5 mol Fe/L) was filtered. After all monomers were dissolved, the monomer solution was filtered, and the filtered solution of iron oxide was added along with 20 ml of a 70 mg/ml ammonium persulfate solution. This resulting solution was rapidly poured into 4 liters of paraffin oil at 60° C. containing 3 ml of Arlacel 83 (sorbitan sesquioleate) and 4 ml of TEMED (N,N,N',N'-tetramethylethylenediamine) under stirring.

The suspension was left for 45 minutes at 60° C. and the microspheres were then recovered by decanting, and washed with 60° C. water and saline solution to remove the excess oil.

Figure 7:
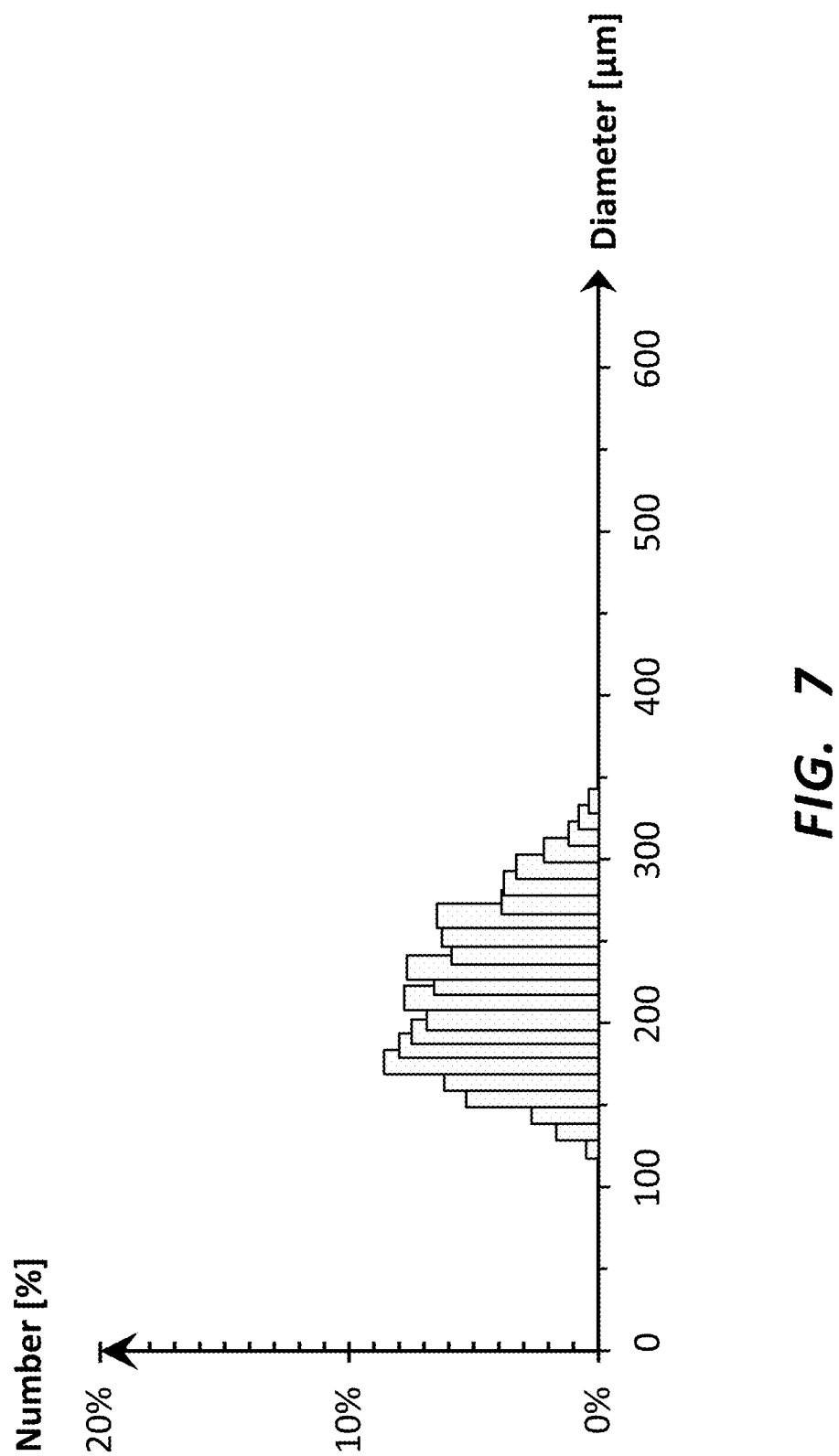
FIG. 7 is a histogram showing the size distribution of microspheres from Example 5.
Figure 8A:
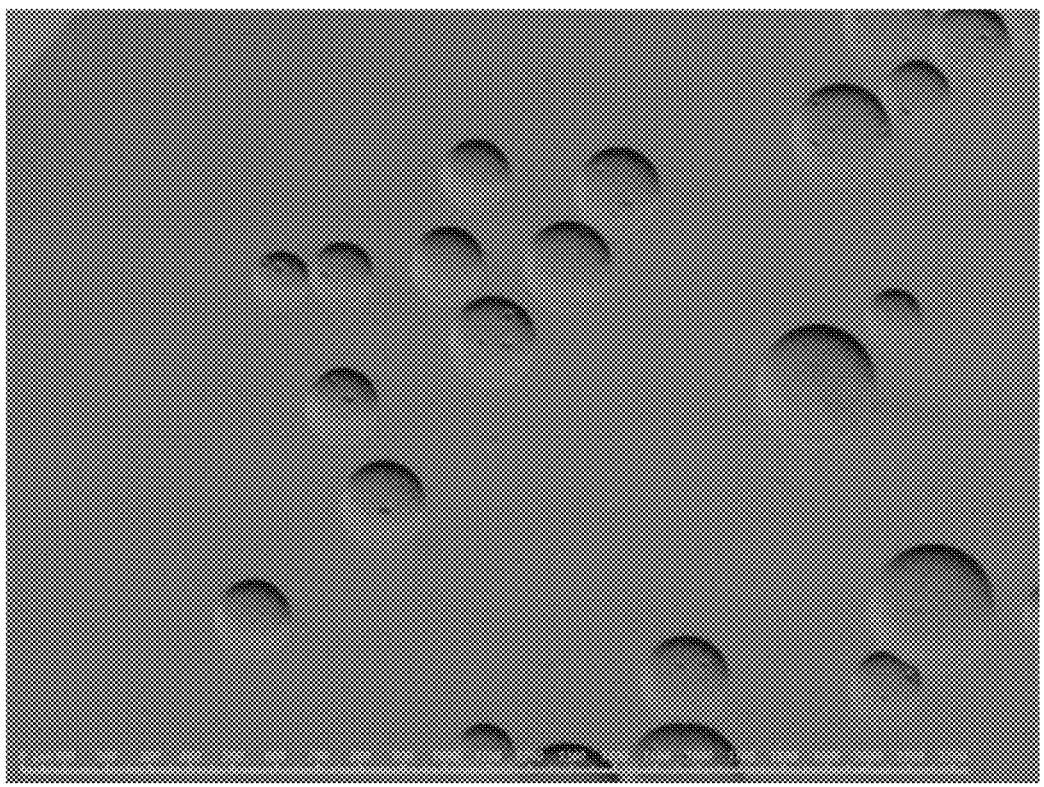
FIGS. 8A, 8B, 8C and 8D are microscope images of microspheres of Example 5.
Figure 8B:
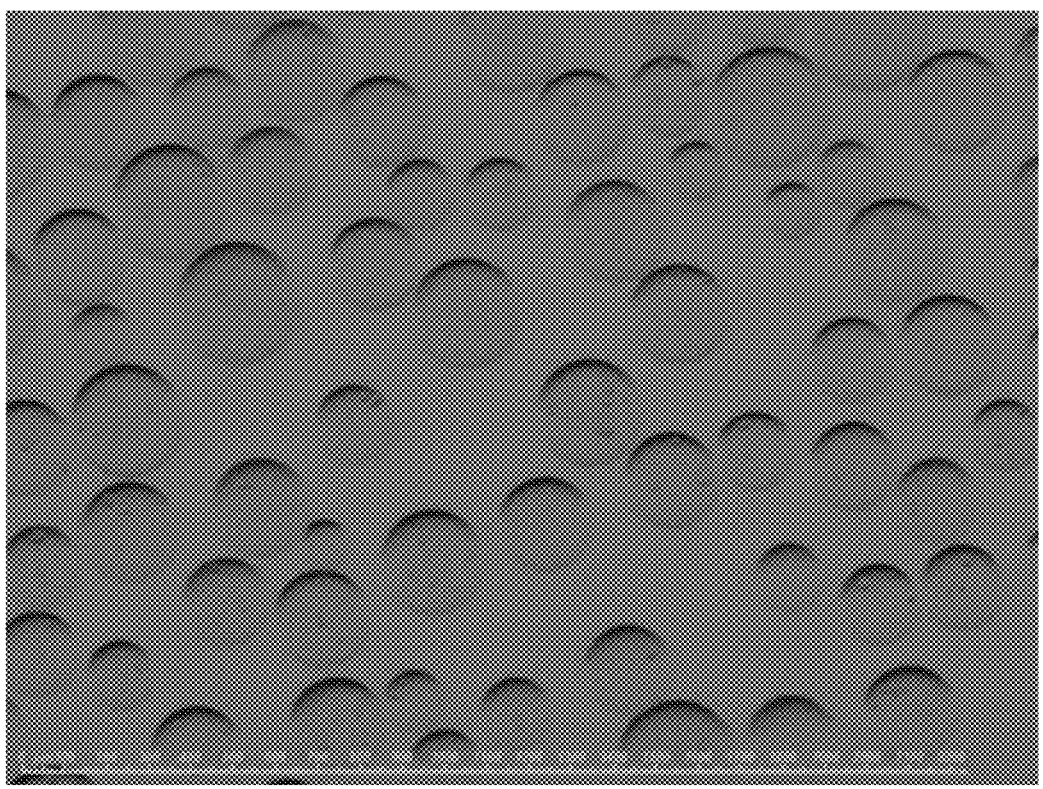
Figure 8C:
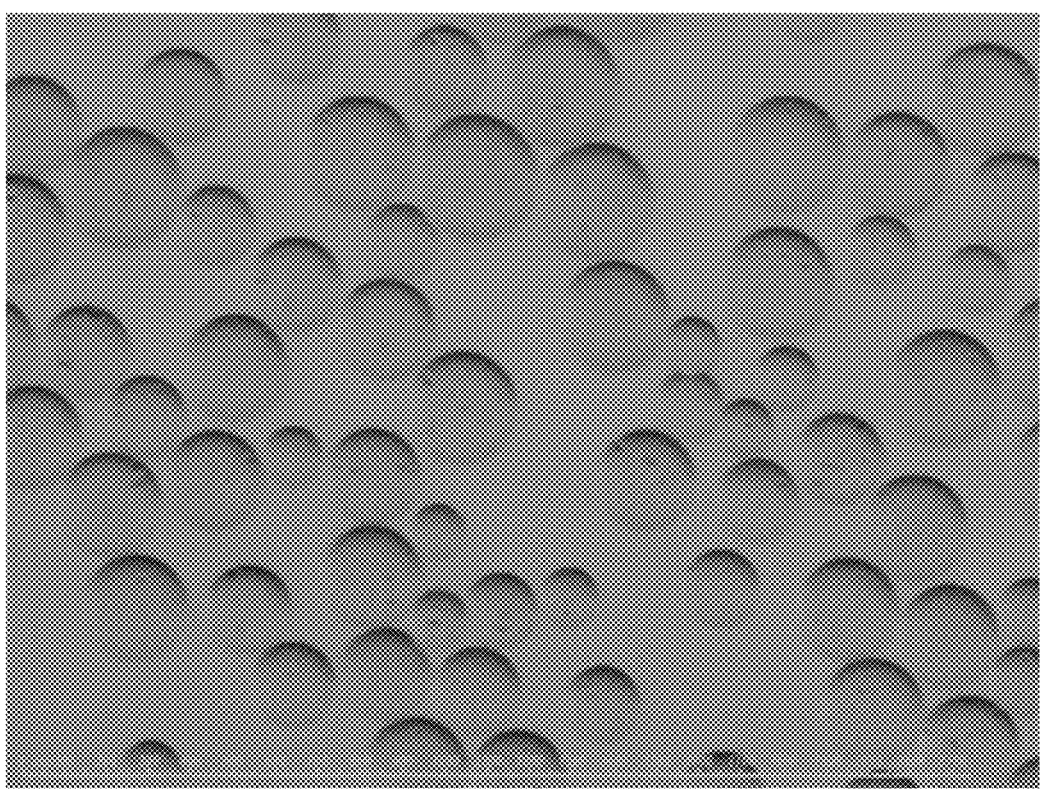
Figure 8D:
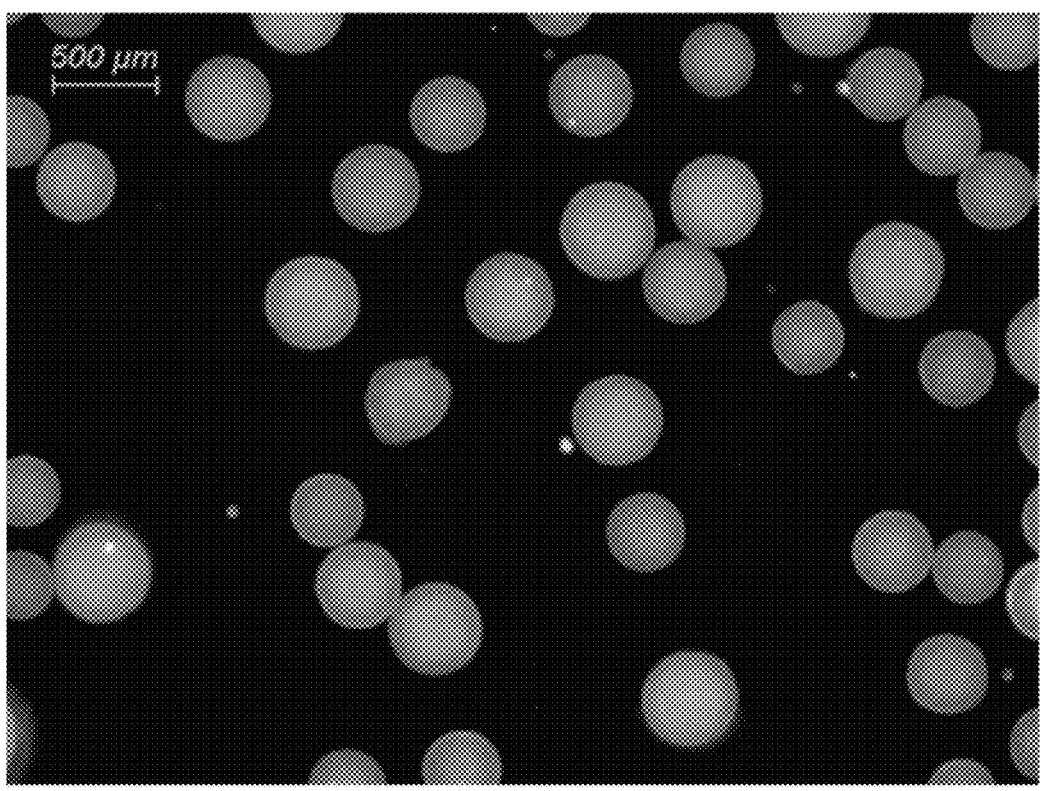

The microspheres were then sieved into different size ranges. The sieved microspheres were then stored in saline. FIG. 7 is a histogram showing the size distribution of microspheres from Example 5. The X axis denotes the size of the microsphere and the Y axis the percentage of microspheres in a given size bin.

Microspheres from Example 5 were subjected to granulometry. As shown, the sieved microspheres formed in Example 5 fall within a particular size distribution of between about 100 μm and about 300 μm. The results of the granulometry experiments are shown in Table 2.

TABLE 2

Characteristics of MRI Detectable Microspheres from Example 5

|  | Number | Minimum | Maximum | Average |
| --- | --- | --- | --- | --- |
| Length [μm] | 1254 | 114.91 | 320.73 | 207.61 |
| Width [μm] |  | 106.11 | 319.72 | 203.66 |

Microspheres from Example 5 were further subjected to microscopy using a microscope linked to a computer for analysis of the images. The microscopy results for Example 5 are shown in FIGS. 8A, 8B, 8C and 8D. As shown in the images, the microspheres formed in Example 5 are substantially spherical.

Example 6—Preparation of MRI-Detectable Microspheres Using AMPS Monomers

In a beaker containing 300 ml of demineralized water, 58 g of sodium chloride and 27 g of sodium acetate were dissolved. Next 400 ml of glycerol was added. Then, 90 g of N-[tris-(hydroxymethyl)methyl]acrylamide, 42.7 g of AMPS and 10 g of N,N-methylene-bis-acrylamide were added. The volume was adjusted to 1 liter by addition of water and the monomer solution was then heated to 50° C.

Separately, a suspension of 25 ml of iron oxide (ferucarbotran—equivalent to 0.5 mol Fe/L) was filtered. After all monomers were dissolved, the pH of the solution was adjusted to between 5.9 and 6.1 with sodium hydroxide. The monomer solution was filtered, and the filtered solution of iron oxide was added along with 20 ml of a 70 mg/ml ammonium persulfate solution. This resulting solution was rapidly poured into 4 liters of paraffin oil at 60° C. containing 3 ml of Arlacel 83 (sorbitan sesquioleate) and 4 ml of TEMED (N,N,N',N'-tetramethylethylenediamine) under stirring.

The suspension was left for 45 minutes at 60° C. and the microspheres were then recovered by decanting, and washed with 60° C. water, and saline solution to remove the excess oil.

Figure 9:
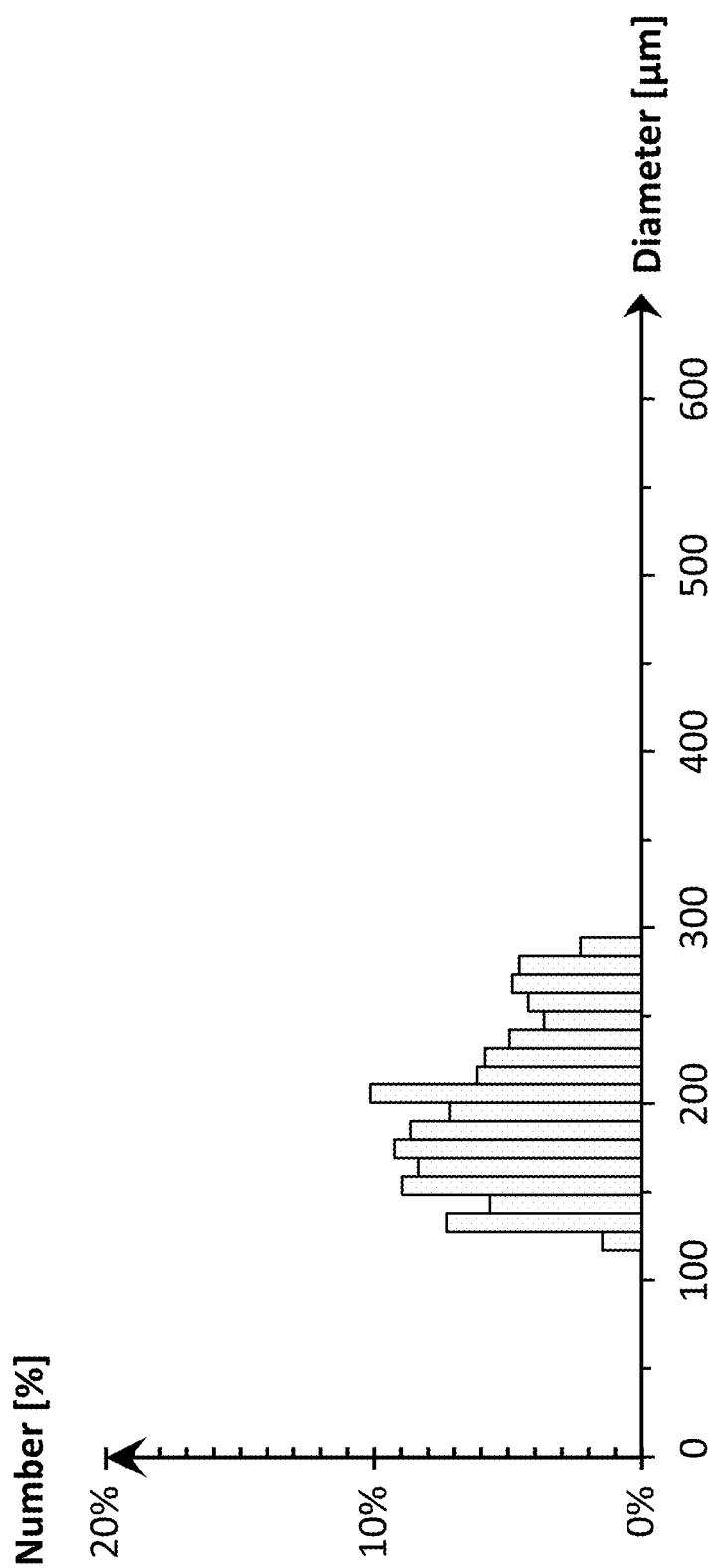
FIG. 9 is a histogram showing the size distribution of microspheres from Example 6.

The microspheres were then sieved into different size ranges. The sieved microspheres were then stored in saline. FIG. 9 is a histogram showing the size distribution of microspheres from Example 6. The X axis denotes the size of the microsphere and the Y axis the percentage of microspheres in a given size bin.

Microspheres from Example 6 were subjected to granulometry. As shown, the sieved microspheres formed in Example 6 fall within a particular size distribution of between about 100 μm and about 300 μm. The results of the granulometry experiments are shown in Table 3.

TABLE 3

Characteristics of MRI Detectable Microspheres from Example 6

|  | Number | Minimum | Maximum | Average |
| --- | --- | --- | --- | --- |
| Length [μm] | 320 | 116.41 | 276.40 | 186.62 |
| Width [μm] |  | 107.88 | 272.51 | 181.36 |

Figure 10A:
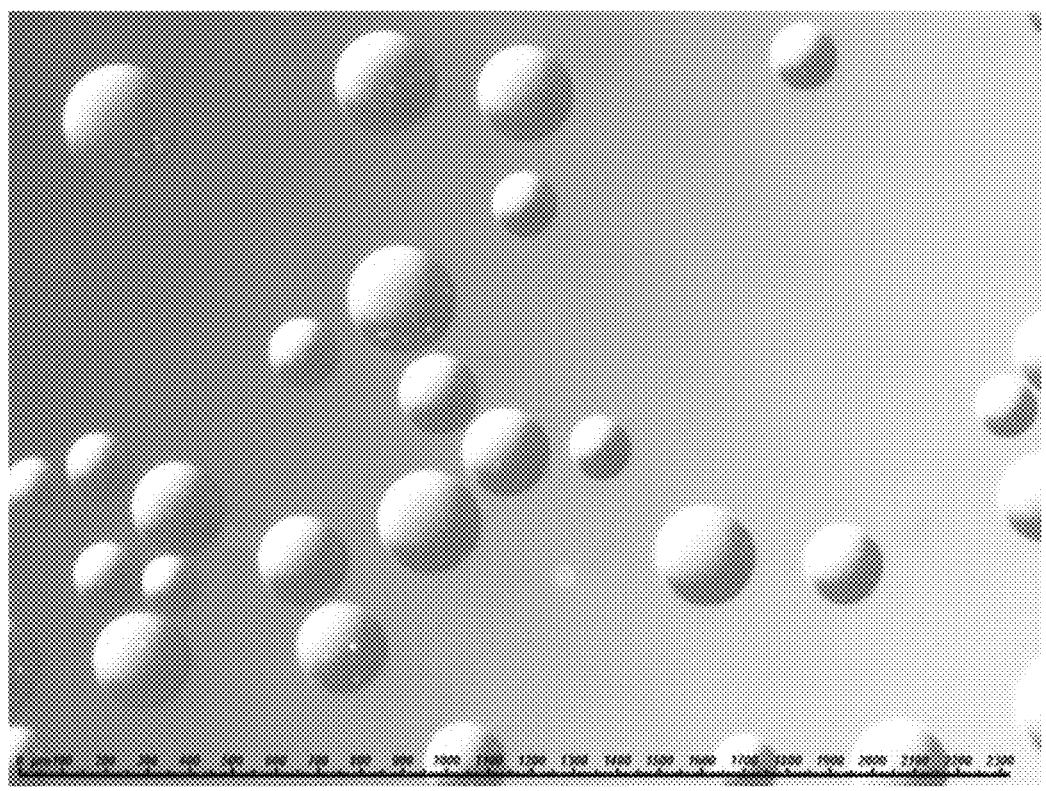
FIGS. 10A and 10B are microscope images of microspheres of Example 6.
Figure 10B:
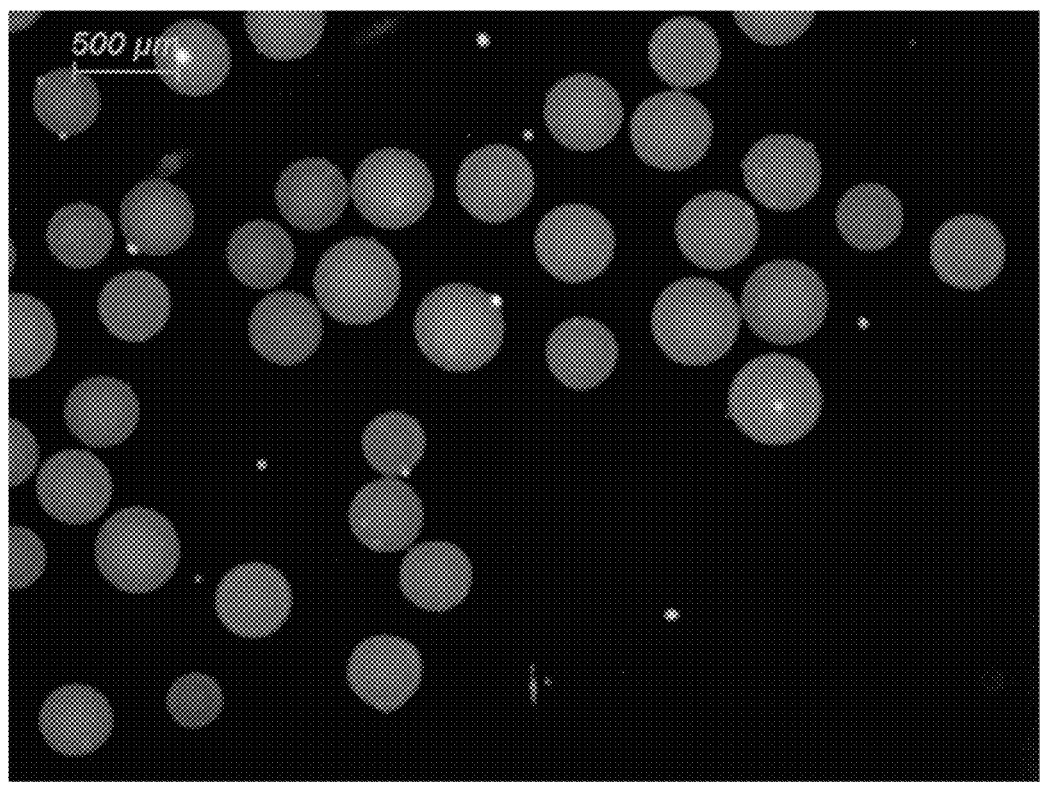

Microspheres from Example 6 were further subjected to microscopy using a microscope linked to a computer for analysis of the images. The microscopy results for Example 6 are shown in FIGS. 10A and 10B. As shown in the images, the microspheres formed in Example 6 are substantially spherical.

Example 7—Preparation of MRI-Detectable Microspheres Using CEA Monomers

In a beaker containing 300 ml of demineralized water, 58 g of sodium chloride and 27 g of sodium acetate were dissolved. Next 400 ml of glycerol was added. Then, 90 g of N-[tris-(hydroxymethyl)methyl]acrylamide, 29.7 g of CEA and 10 g of N,N-methylene-bis-acrylamide were added. The volume was adjusted to 1 liter by addition of water and the monomer solution was then heated to 50° C.

Separately, a suspension of 25 ml of iron oxide (ferucarbotran—equivalent to 0.5 mol Fe/L) was filtered. After all monomers were dissolved, the pH of the solution was adjusted to between 5.9 and 6.1 with sodium hydroxide and acetic acid. The monomer solution was filtered, and the filtered solution of iron oxide was added along with 20 ml of a 70 mg/ml ammonium persulfate solution. This resulting solution was rapidly poured into 4 liters of paraffin oil at 60° C. containing 3 ml of Arlacel 83 (sorbitan sesquioleate) and 4 ml of TEMED (N,N,N',N'-tetramethylethylenediamine) under stirring.

The suspension was left for 45 minutes at 60° C. and the microspheres were then recovered by decanting, and washed with 60° C. water and saline solution to remove the excess oil.

Figure 11:
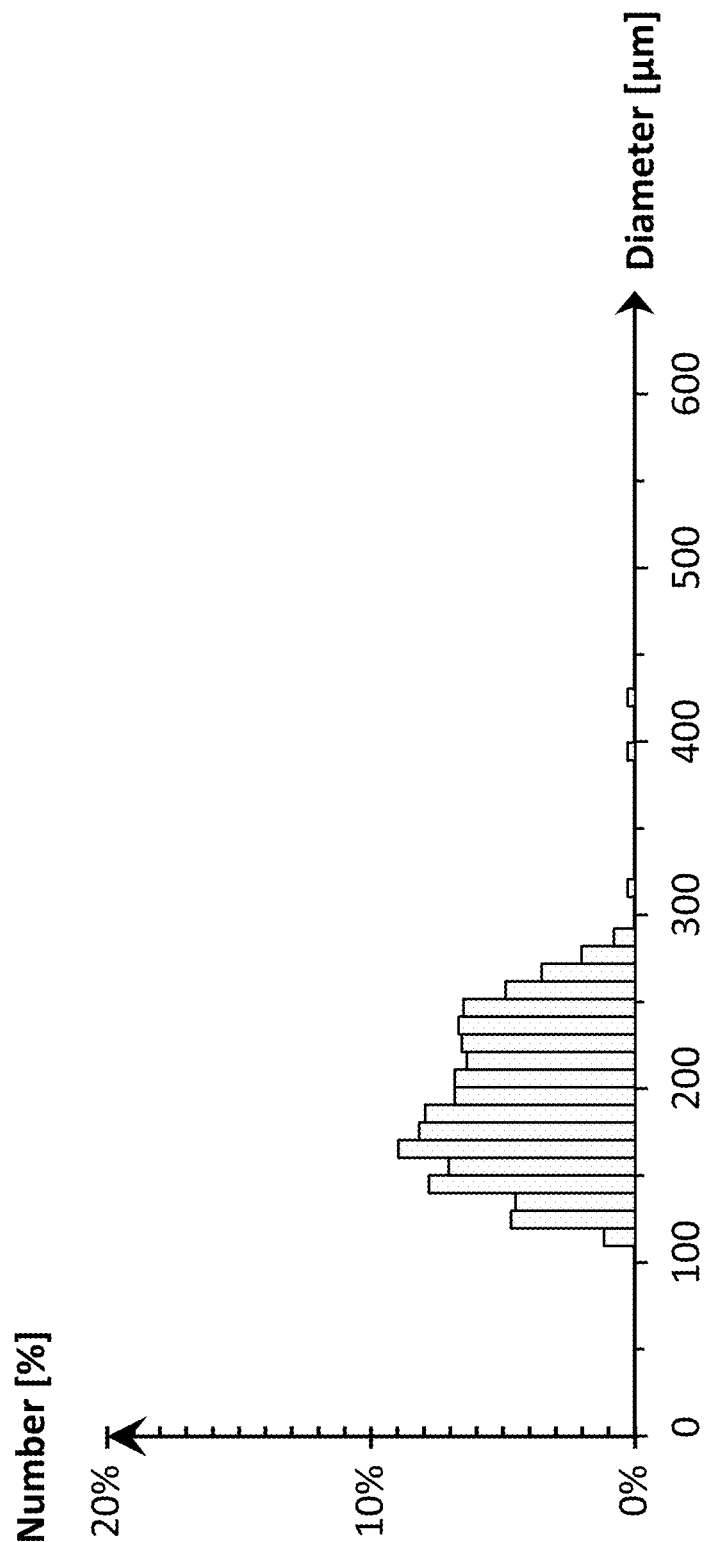
FIG. 11 is a histogram showing the size distribution of microspheres from Example 7.

The microspheres were then sieved into different size ranges. The sieved microspheres were then stored in saline. FIG. 11 is a histogram showing the size distribution of microspheres from Example 7. The X axis denotes the size of the microsphere and the Y axis the percentage of microspheres in a given size bin.

Microspheres from Example 7 were subjected to granulometry. As shown, the sieved microspheres formed in Example 7 fall within a particular size distribution of between about 100 μm and about 300 μm. The results of the granulometry experiments are shown in Table 4.

TABLE 4

Characteristics of MRI Detectable Microspheres from Example 7

|  | Number | Minimum | Maximum | Average |
| --- | --- | --- | --- | --- |
| Length [μm] | 1262 | 101.19 | 410.01 | 183.90 |
| Width [μm] |  | 94.05 | 320.53 | 178.70 |

Figure 12A:
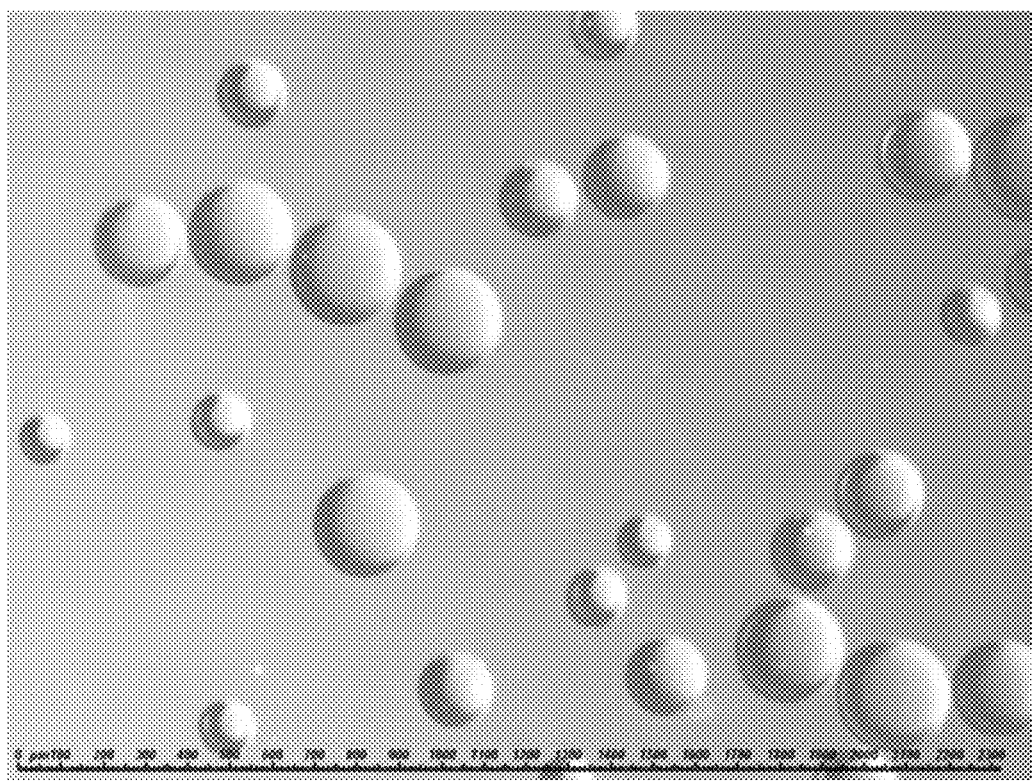
FIGS. 12A and 12B are microscope images of microspheres of Example 7.
Figure 12B:
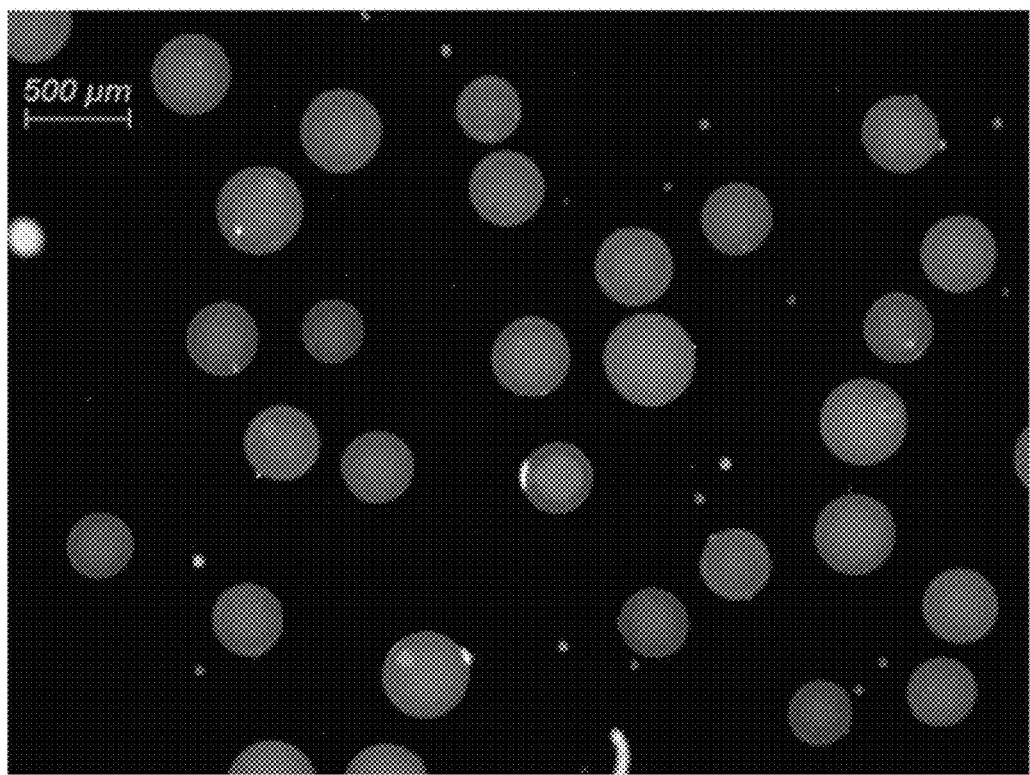

Microspheres from Example 7 were further subjected to microscopy using a microscope linked to a computer for analysis of the images. The microscopy results for Example 9 are shown in FIGS. 12A and 12B. As shown in the images, the microspheres formed in Example 7 are substantially spherical.

Example 8—Drug (Doxorubicin) Loading of MRI Detectable Microspheres of Examples 1, 5, 6 and 7

In vials containing 2 ml of the microspheres synthesized in Examples 1, 5, 6 and 7, the excess supernatant was removed and 8 ml of a doxorubicin (Adriblastin, Pfizer, 50 mg) solution was added to each vial. After addition of doxorubicin, the vials were agitated every minute for the first 10 minutes. Samples of 100 μl of supernatant were drawn from each vial at 15, 30, 45, 60, 90 and 120 minutes.

Figure 13:
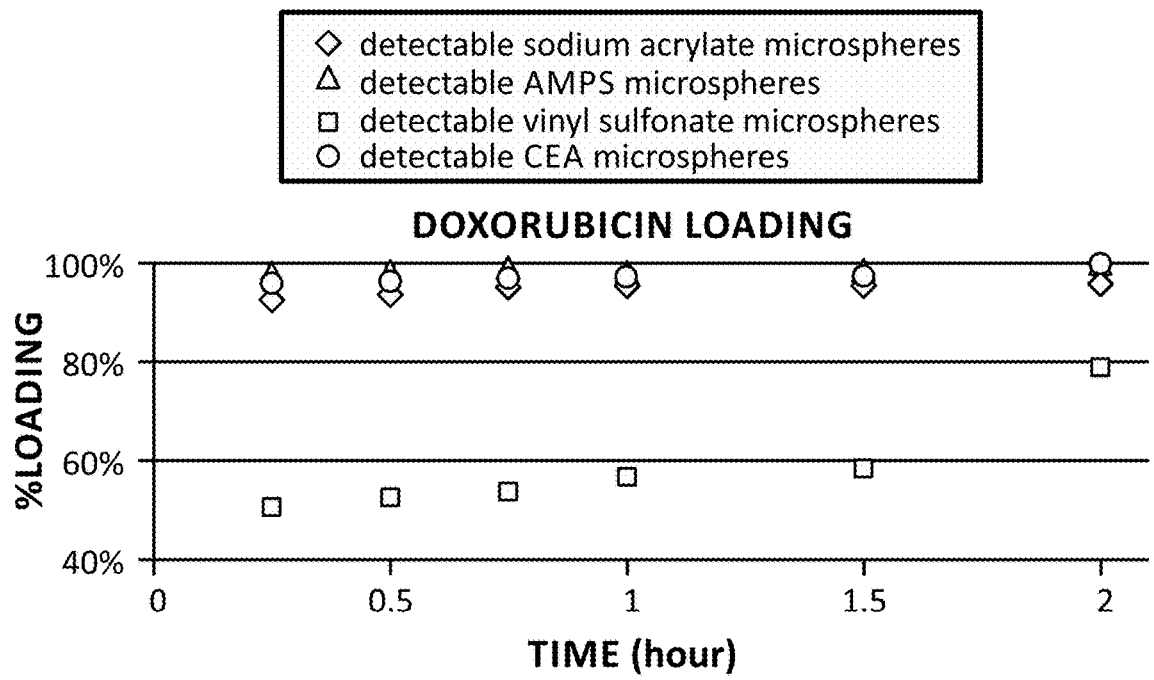
FIG. 13 is a graph depicting the drug loading behavior data collected in Example 8.

The concentration of doxorubicin in the supernatant was analyzed following the procedure described in Example 4. The results of the experiment are shown in FIG. 13. The X axis denotes the amount of time the biomaterials were incubated with the doxorubicin solution, and the Y axis denotes the percentage of doxorubicin in the solution that has become associated with the biomaterials.

Example 9—Drug (Doxorubicin) Release for MRI Detectable Microspheres of Examples 1, 5, 6 and 7

The study was performed at room temperature. Two ml of drug loaded MRI detectable microspheres from Example 8 (after 2 h of loading) were introduced into 500 ml of saline and 10 mM MES (morpholino ethane sulfonic acid) in a beaker. About 100 μl of the supernatant was sampled periodically and the drug content was analysed by HPLC as described in Example 8.

The release was calculated using the following equation:

$$\% \text{ release at time } t = \frac{\text{drug mass in the supernatant at time } t}{\text{initial drug mass}} \times 100$$

with the mass at time t=concentration at time t×volume of solution at time t.

Figure 14:
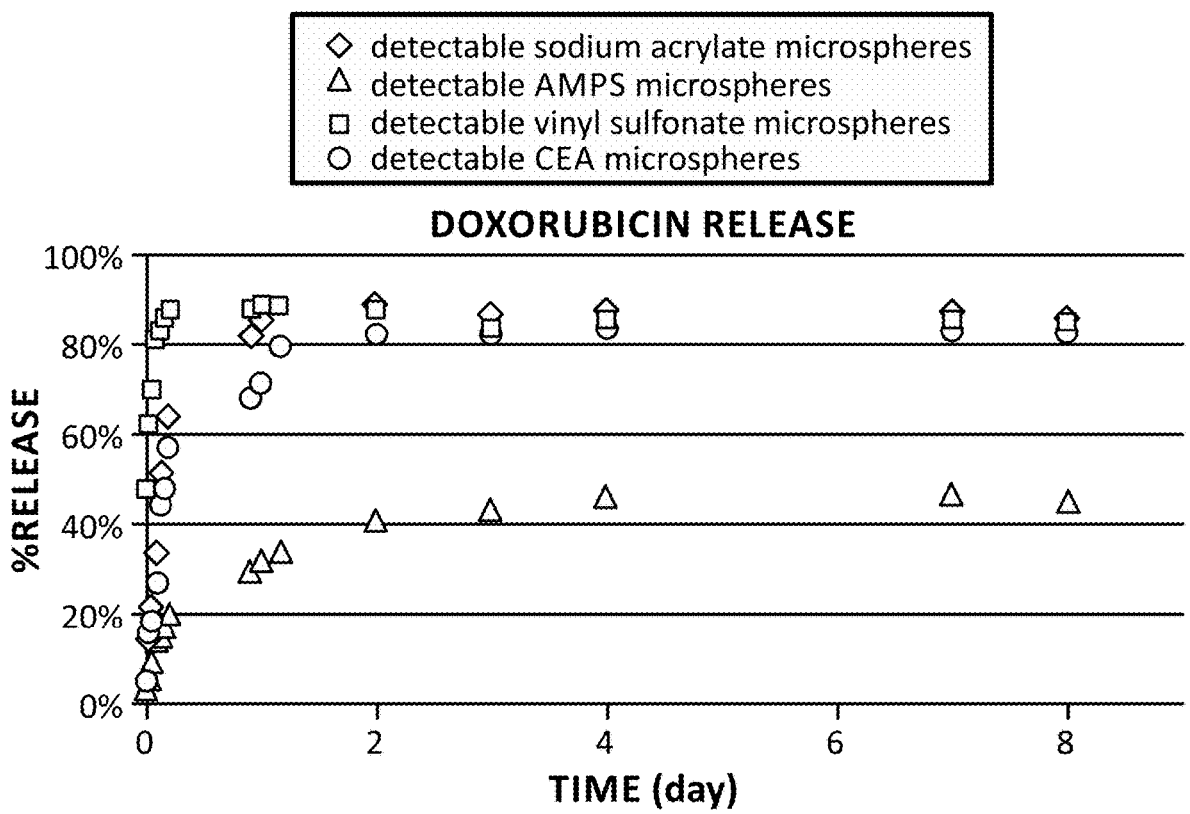
FIG. 14 is a graph depicting the drug release behavior data collected in Example 9.

The results of the experiment are depicted in FIG. 14. The X axis denotes the amount of time the biomaterials were dialyzed, and the Y axis denotes the percentage of doxorubicin originally associated with the biomaterial that has been released from the biomaterials.

Example 10—Drug (Irinotecan) Loading of MRI Detectable Microspheres of Examples 1, 5, 6 and 7

In vials containing 2 ml of the microspheres synthesized in Examples 1, 5, 6 and 7, the excess supernatant was removed and 5 ml of an irinotecan (Campto, Pfizer, 100 mg) solution was added to each vial. After addition of irinotecan, the vials were agitated every minute for the first 10 minutes. Samples of 100 μl of supernatant were drawn from each vial at 15, 30, 45, 60, 90 and 120 minutes.

The concentration of irinotecan in the supernatant was analyzed by reverse phase high performance liquid chromatography (Uptisphere CN Interchim column, 250 mm×4.0 mm). The elution phase consisted in 70% (v/v) water with 0.1% TFA (trifluoro acetic acid), 30% (v/v) acetonitrile. UV detection was at $\lambda_{max}$ 275 nm.

The loading efficiency was calculated using the same equation as in Example 8.

Figure 15:
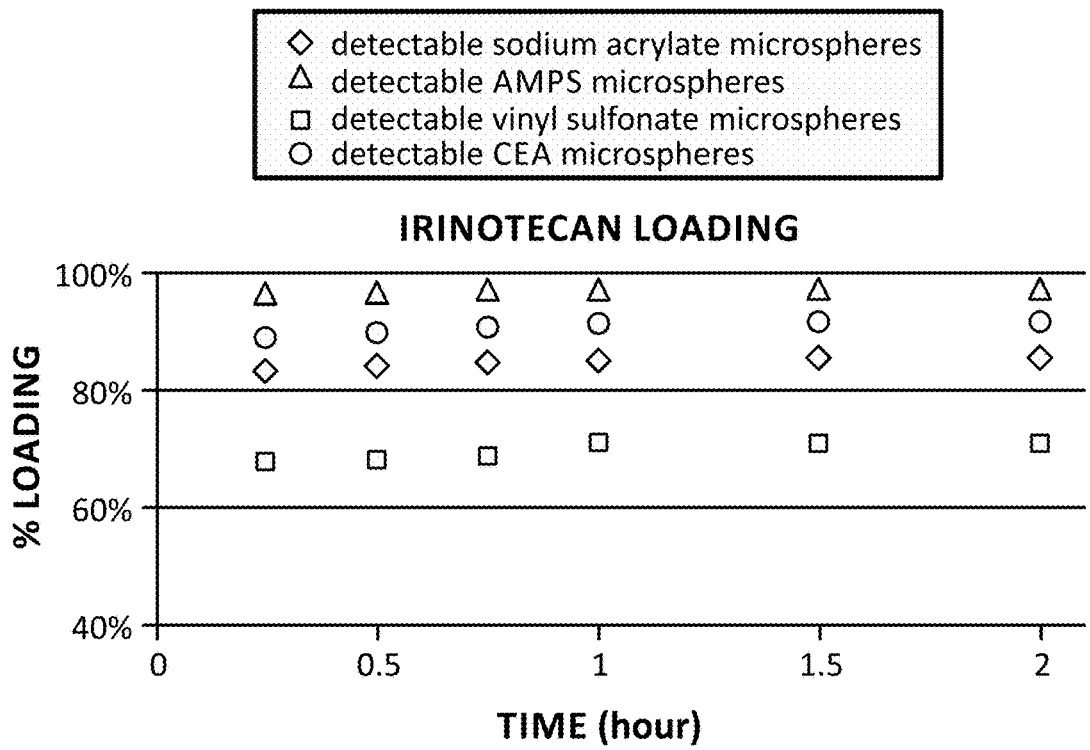
FIG. 15 is a graph depicting the drug loading behavior data collected in Example 10.

The results of the experiment are shown in FIG. 15. The X axis denotes the amount of time the biomaterials were incubated with the irinotecan solution, and the Y axis denotes the percentage of irinotecan in the solution that has become associated with the biomaterials.

Example 11—Drug (Irinotecan) Release Dynamics for MRI Detectable Microspheres of Examples 1, 5, 6 and 7

A dialysis membrane model was used to analyze the release of irinotecan from the microspheres over time, as Example 4.

The study was performed at room temperature. Two ml of drug loaded MRI detectable microspheres from Examples 1, 5, 6 and 7 were introduced into a 12 ml dialysis membrane (Slide-A-Lyzer, Thermo Fisher-MWCO 20,000 Da), which was then introduced in a 600 ml graduated beaker filled with 500 ml of saline under slow stirring. About 100 μl of the saline solution was sampled periodically from the 500 ml reservoir and the drug content was analysed by HPLC as described in Example 10.

The release was calculated using the same equation as in Example 9.

Figure 16:
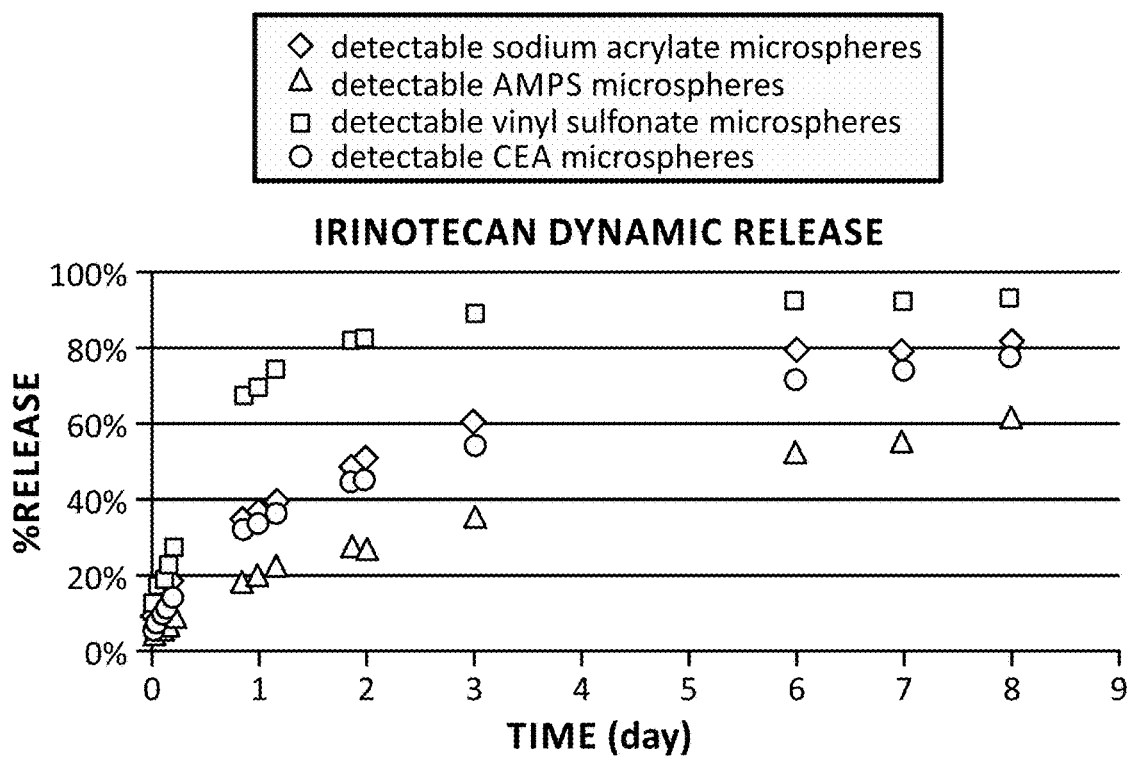
FIG. 16 is a graph depicting the drug release behavior data collected in Example 11.

The results of the experiment are depicted in FIG. 16. The X axis denotes the amount of time the biomaterials were dialyzed, and the Y axis denotes the percentage of irinotecan originally associated with the biomaterial that has been released from the biomaterials.

It will be obvious to those having skill in the art that many changes may be made to the details of the above-described embodiments without departing from the underlying principles of the invention. The scope of the present invention should, therefore, be determined only by the following claims.

The invention claimed is:

1. A biomaterial suitable for use as a drug eluting, Magnetic Resonance Imaging ("MRI") detectable implant for vascular occlusion, comprising:
   a copolymer comprising N-[tris-(hydroxymethyl)methyl] acrylamide and vinyl sulfonate;
   an iron oxide particle; and
   a drug.

2. The biomaterial of claim 1, wherein the biomaterial is in the form of substantially spherical microspheres.

3. The biomaterial of claim 2, wherein the microspheres have an average major axis of from about 15 micrometers to about 1000 micrometers.

4. The biomaterial of claim 1, wherein the biomaterial further comprises N,N-methylene-bis-acrylamide.

5. The biomaterial of claim 1, wherein the copolymer further comprises a crosslinking agent.

6. The biomaterial of claim 1, wherein the drug is a chemotherapeutic drug.

7. The biomaterial of claim 6, wherein the drug is at least one of doxorubicin or irinotecan.

8. The biomaterial of claim 1, wherein the biomaterial comprises 5 wt % to 50 wt % of vinyl sulfonate.

9. The biomaterial of claim 2, wherein the drug is releasably associated with the microsphere.

10. The biomaterial of claim 1, wherein the iron oxide particle comprises $Fe_3O_4$.

11. The biomaterial of claim 1, wherein the iron oxide particle comprises colloidal iron.

12. A biomaterial suitable for use as a drug eluting, Magnetic Resonance Imaging ("MRI") detectable implant for vascular occlusion, comprising:
   a copolymer comprising N-[tris-(hydroxymethyl)methyl] acrylamide and 2-carboxyethyl acrylate ("CEA");
   an iron oxide particle; and
   a drug.

13. The biomaterial of claim 12, wherein the biomaterial is in the form of substantially spherical microspheres.

14. The biomaterial of claim 12, wherein the biomaterial further comprises N,N-methylene-bis-acrylamide.

15. The biomaterial of claim 12, wherein the copolymer further comprises a crosslinking agent.

16. The biomaterial of claim 12, wherein the drug is at least one of doxorubicin or irinotecan.

17. The biomaterial of claim 12, wherein the biomaterial comprises 5 wt % to 50 wt % of CEA.

18. The biomaterial of claim 13, wherein the drug is releasably associated with the microsphere.

19. The biomaterial of claim 12, wherein the iron oxide particle comprises $Fe_3O_4$.

20. The biomaterial of claim 12, wherein the iron oxide particle comprises colloidal iron.

* * * * *